United States Patent
Cox et al.

(10) Patent No.: US 10,765,625 B2
(45) Date of Patent: Sep. 8, 2020

(54) KNOTTIN-DRUG CONJUGATES AND METHODS OF USING THE SAME

(71) Applicant: THE BOARD OF TRUSTEES OF THE LELAND STANFORD JUNIOR UNIVERSITY, Stanford, CA (US)

(72) Inventors: Nicholas Cox, Seattle, WA (US); Jennifer R. Cochran, Stanford, CA (US); Mark Smith, San Francisco, CA (US); James R. Kintzing, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 8 days.

(21) Appl. No.: 15/458,852

(22) Filed: Mar. 14, 2017

(65) Prior Publication Data

US 2017/0304342 A1    Oct. 26, 2017

Related U.S. Application Data

(60) Provisional application No. 62/308,753, filed on Mar. 15, 2016.

(51) Int. Cl.

| | |
|---|---|
| *A61K 9/00* | (2006.01) |
| *A61K 47/00* | (2006.01) |
| *C07K 14/47* | (2006.01) |
| *A61K 47/64* | (2017.01) |
| *A61K 47/65* | (2017.01) |
| *A61K 31/7068* | (2006.01) |
| *A61K 47/42* | (2017.01) |
| *A61K 38/00* | (2006.01) |

(52) U.S. Cl.
CPC .......... *A61K 9/0019* (2013.01); *A61K 9/0053* (2013.01); *A61K 31/7068* (2013.01); *A61K 47/00* (2013.01); *A61K 47/64* (2017.08); *A61K 47/65* (2017.08); *C07K 14/4702* (2013.01); *A61K 38/00* (2013.01); *A61K 47/42* (2013.01)

(58) Field of Classification Search
CPC .. A61K 9/0019; A61K 31/7068; A61K 38/00; A61K 47/00; A61K 47/42; A61K 47/64; A61K 47/65; A61K 9/0053; C07K 14/4702
See application file for complete search history.

(56) References Cited

U.S. PATENT DOCUMENTS

| | | | | |
|---|---|---|---|---|
| 7,585,491 | B2 * | 9/2009 | Govindan | C07K 16/2803 |
| | | | | 424/1.49 |
| 9,562,049 | B2 * | 2/2017 | Howard | C07D 487/04 |
| 9,587,001 | B2 * | 3/2017 | Cochran | C07K 14/811 |
| 2009/0155275 | A1 * | 6/2009 | Wu | C07K 16/468 |
| | | | | 424/136.1 |
| 2009/0257952 | A1 * | 10/2009 | Cochran | A61K 38/1709 |
| | | | | 424/1.69 |
| 2015/0266936 | A1 | 9/2015 | Cochran et al. | |

FOREIGN PATENT DOCUMENTS

| | | |
|---|---|---|
| WO | 2008045252 A2 | 4/2008 |
| WO | 2012064658 A1 | 5/2012 |
| WO | 2014063012 A1 | 4/2014 |

OTHER PUBLICATIONS

Andrews, Whole brain radiation therapy with or without stereotactic radiosurgery boost for patients with one to three brain metastases: phase III results of the RTOG 9508 randomised trial, 2004, The Lancet, vol. 363.*
Kimura, Engineered Knottin Peptides: A New Class of Agents for Imaging Integrin Expression in Living Subjects, Cancer Res. 2009, 69(6): 2435-2442 (Year: 2009).*
Jordheim, Advances in the development of nucleoside and nucleotide analogues for cancer and viral diseases, Nature Reviews 2013, vol. 12 (Year: 2013).*
Glotzbach, Combinatorial Optimization of Cystine-Knot Peptides towards High-Affinity Inhibitors of Human Matriptase-1, PLOS One 2013, vol. 10 (Year: 2013).*
Kim, Protein conjugation with genetically encoded unnatural amino acids. Curr Opin Chem Biol. 2013, 17(3): 412-419 (Year: 2013).*
Sankaran (Supramolecular Surface Immobilization of Knottin Derivatives for Dynamic Display of High Affinity Binders, Bioconjugate Chemistry 2015, 26:1972-1980) (Year: 2015).*
Kimura (Engineered Knottin Peptides: A New Class of Agents for Imaging Integrin Expression in Living Subjects, Cancer Res. 2009, 69(6): 2435-2442, of record) (Year: 2009).*
Jordheim (Advances in the development of nucleoside and nucleotide analogues for cancer and viral diseases, Nature Reviews 2013, vol. 12, of record) (Year: 2013).*
Glotzbach (Combinatorial Optimization of Cystine-Knot Peptides towards High-Affinity Inhibitors of Human Matriptase-1, PLOS One 2013, vol. 10, of record). (Year: 2013).*

(Continued)

*Primary Examiner* — Marcela M Cordero Garcia
(74) *Attorney, Agent, or Firm* — Brian E. Davy; Bozicevic, Field & Francis LLP

(57) ABSTRACT

Provided are knottin-drug conjugates. The conjugates include a knottin peptide that includes an engineered loop that binds to a target on a cancer cell surface, and a drug (e.g., a nucleoside drug) conjugated to the knottin peptide through a linker. Also provided are pharmaceutical compositions and kits that include the knottin-drug conjugates, as well as methods of using the knottin-drug conjugates, e.g., for therapeutic purposes.

33 Claims, 10 Drawing Sheets
Specification includes a Sequence Listing.

(56) References Cited

OTHER PUBLICATIONS

Kim (Protein conjugation with genetically encoded unnatural amino acids. Curr Opin Chem Biol. 2013, 17(3): 412-419, of record) Year: 2013).*

Zhong et al. Cathepsin B-cleavable dosxorubicin prodrugs for targeted cancer therapy (Reveiw). International Journal of Oncology. vol. 42, pp. 373-383. (Year: 2013).*

Zhang et al. Enzyme-responsive peptide dendrimer-gemcitabine conjugate as a controlled-release drug delivery vehicle with enhanced antitumor efficacy. Acta Biomaterialia. vol. 55, pp. 153-162 (Year: 2017).*

Ackerman et al. (2014) "Cystine-knot peptides: emerging tools for cancer imaging and therapy" Expert Review Proteomics 11(5):561-572.

Cox et al. "Engineered knottin peptide-drug conjugates selectively deliver small molecules to brain tumors in mice" Abstract 438, 251st American Chemical Society National Meeting & Exposition, Mar. 13-17, 2016, San Diego, CA, accessed online Mar. 11, 2016.

Lahti et al. (2009) "Interrogating and Predicting Tolerated Sequence Diversity in Protein Folds: Application to E. elaterium Trypsin Inhibitor-II Cystine-Knot Miniprotein" PLoS Comput. Biol. 5(9): e1000499.

Maab et al. (2015) "Cystine-knot peptides targeting cancer-relevant human cytotoxic T lymphocyte-associated antigen 4 (CTLA-4)" Journal of Peptide Science, Online Article DOI: 10.1002/psc.2782.

Quinn et al. (2016) "Therapy of pancreatic cancer via an EphA2 receptor-targeted delivery of gemcitabine" Oncotarget; 7(13): 17103-17110.

* cited by examiner

GCPRPRGDNPPLTCXQDSDCLAGCVCGPNGFCG

| Knottin | X | IC$_{50}$ in U87MG |
|---|---|---|
| EETI-2.5F (1) | serine | 1.1 ± 0.2 nM |
| EETI-2.5Z (2) | 5-azido-L-norvaline | 1.1 ± 1.8 nM |

KNOTTIN-DRUG CONJUGATES AND METHODS OF USING THE SAME

CROSS-REFERENCE TO RELATED APPLICATIONS

This application claims the benefit of U.S. Provisional Patent Application No. 62/308,753 filed Mar. 15, 2016, which application is incorporated herein by reference in its entirety.

STATEMENT REGARDING FEDERALLY SPONSORED RESEARCH

This invention was made with Government support under contract NS075144 awarded by the National Institutes of Health. The Government has certain rights in the invention.

INTRODUCTION

Traditional approaches to cancer treatment chemotherapy involve the administration of small molecules designed to inhibit tumor growth or metastasis, often using small drug molecules that are cytotoxic to cancer cells, disrupt signaling necessary for cancer growth, or activate the immune system. These compounds often do not distinguish between cancer and healthy cells or tissues, often resulting in severe side-effects from cancer treatment. In addition, for many types of tumor, such as those occurring in cases of brain or pancreatic cancers, chemotherapeutic small molecules are limited in their ability to diffuse into the tumor or into individual cancer cells, and thus their therapeutic value is significantly limited. Recent advances in antibody-drug conjugate technology have enabled small molecule drug payloads to be delivered selectively to tumor cells, mediated by the high affinity of the antibody scaffold for a target receptor that is over-expressed in a cancer.

Cystine-knot miniproteins, also known as knottins, are a structural family (typically 30-50 amino acids in length) characterized by a core of antiparallel β-strands stabilized by at least three disulfide bonds. In a characteristic cystine-knot motif, the first and fourth and the second and fifth cysteine residues form disulfide bonds. A disulfide bond formed between the third and sixth cysteine residues passes through these first two disulfides, creating a macrocyclic knot. This disulfide-constrained core confers chemical, thermal and proteolytic stability upon the peptide.

Knottins also possess loop regions of variable length and composition that are constrained to the core of antiparallel β-strands. These loops are important for folding, structural integrity, molecular recognition and biological function. The loop regions of knottin peptides have been shown to tolerate amino acid mutations. In contrast to linear peptides, knottins have been shown to retain their three-dimensional structure and function after boiling or incubation in acid, base and serum.

Polypeptides containing cysteine-knot motifs are found in a variety of fungi, plants and animals, and carry out diverse functions including protease inhibition, ion channel blockade and antimicrobial activity. As examples, toxins from scorpions, spiders and snails block ion channel activity, the Ecballium elaterium trypsin inhibitor II (EETI-II) from plants inhibits serine proteases and the human Agouti-Related Protein (AgRP) is a regulatory neuropeptide.

SUMMARY

Provided are knottin-drug conjugates. The conjugates include a knottin peptide that includes an engineered loop that binds to a target on a cancer cell surface, and a drug (e.g., a nucleoside drug) conjugated to the knottin peptide through a linker. Also provided are pharmaceutical compositions and kits that include the knottin-drug conjugates, as well as methods of using the knottin-drug conjugates, e.g., for therapeutic purposes.

BRIEF DESCRIPTION OF THE FIGURES

FIG. 10 shows that integrin-blocking with 1 does not decrease potency of 5a.

DETAILED DESCRIPTION

Figures 1, 2:
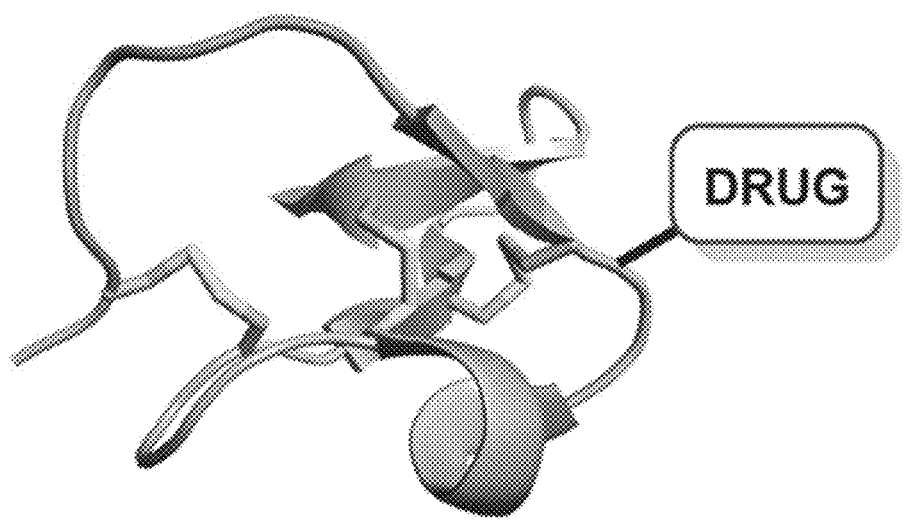
FIG. 1 schematically illustrates a knottin-drug conjugate for tumor-targeted drug delivery.
FIG. 2 shows the sequences of knottin peptides EETI 2.5F and EETI 2.5Z with integrin-binding loop (PRPRGDN-PPLT) and disulfide linkages of the cysteine-knot scaffold shown.

Provided are knottin-drug conjugates. The conjugates include a knottin peptide that includes an engineered loop that binds to a target on a cancer cell surface, and a drug (e.g., a nucleoside drug) conjugated to the knottin peptide through a linker. Also provided are pharmaceutical compositions and kits that include the knottin-drug conjugates, as well as methods of using the knottin-drug conjugates, e.g., for therapeutic purposes.

Before the conjugates, compositions, and methods of the present disclosure are described in greater detail, it is to be understood that the conjugates, compositions, and methods are not limited to particular embodiments described, as such may, of course, vary. It is also to be understood that the terminology used herein is for the purpose of describing particular embodiments only, and is not intended to be limiting, since the scope of the conjugates, compositions, and methods will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the conjugates, compositions, and methods. The upper and lower limits of these smaller ranges may independently be included in the smaller ranges and are also encompassed within the conjugates, compositions, and methods, subject to any specifically excluded limit in the stated range. Where the stated range includes one or both of the limits, ranges excluding either or both of those included limits are also included in the conjugates, compositions, and methods.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which the conjugates, compositions, and methods belong. Although any conjugates, compositions, and methods similar or equivalent to those described herein can also be used in the practice or testing of the conjugates, compositions, and methods, representative illustrative conjugates, compositions, and methods are now described.

All publications and patents cited in this specification are herein incorporated by reference as if each individual publication or patent were specifically and individually indicated to be incorporated by reference and are incorporated herein by reference to disclose and describe the materials and/or methods in connection with which the publications are cited. The citation of any publication is for its disclosure prior to the filing date and should not be construed as an admission that the present conjugates, compositions, and methods are not entitled to antedate such publication, as the date of publication provided may be different from the actual publication date which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the conjugates, compositions, and methods, which are, for clarity, described in the context of separate embodiments, may also be provided in combination in a single embodiment. Conversely, various features of the conjugates, compositions, and methods, which are, for brevity, described in the context of a single embodiment, may also be provided separately or in any suitable sub-combination. All combinations of the embodiments are specifically embraced by the present disclosure and are disclosed herein just as if each and every combination was individually and explicitly disclosed, to the extent that such combinations embrace operable processes and/or compositions. In addition, all sub-combinations listed in the embodiments describing such variables are also specifically embraced by the present conjugates, compositions, and methods and are disclosed herein just as if each and every such sub-combination was individually and explicitly disclosed herein.

As will be apparent to those of skill in the art upon reading this disclosure, each of the individual embodiments described and illustrated herein has discrete components and features which may be readily separated from or combined with the features of any of the other several embodiments without departing from the scope or spirit of the present methods. Any recited method can be carried out in the order of events recited or in any other order that is logically possible.

Knottin-Drug Conjugates

As summarized above, aspects of the present disclosure include knottin-drug conjugates. The conjugates include a knottin peptide that includes an engineered loop that binds to a target on a cancer cell surface, and a drug (e.g., a nucleoside drug) conjugated to the knottin peptide through a linker. These components of the conjugates will now be described in detail.

Knottin Peptides

The type of knottin peptide employed in the conjugates of the present disclosure may vary. The three-dimensional structure of a knottin peptide is minimally defined by a particular arrangement of three disulfide bonds. This characteristic topology forms a molecular knot in which one disulfide bond passes through a macrocycle formed by the other two intra-chain disulfide bridges. Although their secondary structure content is generally low, knottins share a small triple-stranded antiparallel β-sheet, which is stabilized by the disulfide bond framework. Folding and functional activity of knottins are often mediated by loop regions that are diverse in both length and amino acid composition. While three disulfide bonds are the minimum number that defines the fold of this family of peptides, knottins can also contain additional cysteine residues, yielding molecules with four or more disulfide bonds and additional constrained loops in their structure. The term "cystine" refers to a Cys residue in which the sulfur group is linked to another amino acid though a disulfide linkage; the term "cysteine" refers to the —SH ("half cystine") form of the residue. Binding loop portions may be adjacent to cystines, such that there are no other intervening cystines in the primary sequence in the binding loop.

The knottin peptide may be a peptide described in the online KNOTTIN database, which includes detailed amino acid sequence, structure, classification and function information for thousands of polypeptides identified as contain cystine-knot motifs. Knottins are found in a variety of plants, animals, insects and fungi.

The knottin peptide may be full-length (that is, the length of the wild-type peptide/polypeptide), the knottin peptide may be truncated relative to the length of the wild-type peptide/polypeptide, or the knottin peptide may include additional amino acids such that the peptide is greater in length relative to the length of the wild-type peptide/polypeptide.

According to certain embodiments, a knottin-drug conjugate (KDC) of the present disclosure includes a knottin peptide based on any one of an Ecballium elaterium trypsin inhibitor II (EETI-II) peptide, an agouti-related protein (AgRP) peptide, a w-conotoxin peptide, a Kalata B1 peptide, an MCoTI-II peptide, an agatoxin peptide, or a chlorotoxin peptide. In some embodiments, the knottin peptide is based on an Ecballium elaterium trypsin inhibitor II (EETI-II) peptide. In some embodiments, the knottin peptide is based on an agouti-related protein (AgRP) peptide.

By "EETI" is meant Protein Data Bank Entry (PDB) 2ETI. Its entry in the KNOTTIN database is EETI-II. In certain aspects, a knottin peptide of a conjugate of the present disclosure is based on an EETI-II peptide having the following amino acid sequence:

(SEQ ID NO: 1)
GCPRILMRCKQDSDCLAGCVCGPNGFCG

By "AGRP" is meant PDB entry 1 HYK and KNOTTIN database entry SwissProt AGRP_HUMAN. AGRP is a 132 amino acid neuropeptide that binds to melanocortin receptors in the human brain and is involved in regulating metabolism and appetite. The biological activity of AgRP is mediated by its C-terminal cysteine knot domain, which contains five disulfide bonds, but a fully active 34 amino acid truncated AgRP that contains only four disulfide bonds has been developed. In certain aspects, a knottin peptide of a conjugate of the present disclosure is based on a truncated AGRP peptide having the following amino acid sequence:

(SEQ ID NO: 2)
CVRLHESCLGQQVPCCDPAATCYCRFFNAFCYCR

According to certain embodiments, a knottin peptide of a conjugate of the present disclosure is based on a Kalata B1 peptide having the following amino acid sequence:

(SEQ ID NO: 3)
CGETCVGGTCNTPGCTCSWPVCTRNGLPV

In certain aspects, a knottin peptide of a conjugate of the present disclosure is based on a MCoTI-II peptide having the following amino acid sequence:

(SEQ ID NO: 4)
SGSDGGVCPKILKKCRRDSDCPGACICRGNGYCG

According to certain embodiments, a knottin peptide of a conjugate of the present disclosure is based on a chlorotoxin peptide having the following amino acid sequence:

(SEQ ID NO: 5)
MCMPCFTTDHQMARKCDDCCGGKGRGKCYGPQCLCR

Sequences and structural (e.g., loop) information for EETI-II, AgRP, w-conotoxin, Kalata B1, MCoTI-II, agatoxin, chlorotoxin, and other knottin peptides upon which the knottin peptides of the conjugates of the present disclosure may be based may be found in the PDB, the KNOTTIN database, and other protein databases.

The knottin peptide includes an engineered loop that binds to a target on a cancer cell surface, cancer associated vasculature, or both. Knottins contain three disulfide bonds interwoven into a molecular 'knot' that constrain loop regions to a core of anti-parallel β-sheets. Wild-type EETI, for example, is composed of 28 amino acids with three disulfide-constrained loops: loop 1 (the trypsin binding loop, residues 3-8), loop 2 (residues 10-14), and loop 3 (residues 22-26) Knottin family members, which include protease inhibitors, toxins, and antimicrobials, share little sequence homology apart from their core cysteine residues. As a result, their disulfide-constrained loops tolerate much sequence diversity, making knottins amenable for protein engineering applications where mutations need to be introduced into a protein without abolishing its three-dimensional fold.

The engineered loop may include amino acid substitutions, insertions, and/or deletions in an existing loop of the knottin peptide, or the engineered loop may be a loop added to the knottin protein. That is, the knottin peptide of the conjugate may include a loop in addition to the one or more loops present in the wild-type peptide. By combining directed evolution with computational covariance analysis, guidelines for introducing modifications (both in amino acid sequence and loop length) into the loop regions of the knottin scaffold have been elucidated. See, e.g., Lahti et al. (2009) *PLoS Comput. Biol.* 5(9): e1000499.

By "cancer cell" is meant a cell exhibiting a neoplastic cellular phenotype, which may be characterized by one or more of, for example, abnormal cell growth, abnormal cellular proliferation, loss of density dependent growth inhibition, anchorage-independent growth potential, ability to promote tumor growth and/or development in an immunocompromised non-human animal model, and/or any appropriate indicator of cellular transformation. "Cancer cell" may be used interchangeably herein with "tumor cell", "malignant cell" or "cancerous cell", and encompasses cancer cells of a solid tumor, a semi-solid tumor, a primary tumor, a metastatic tumor, and the like.

The engineered loop confers upon the knottin peptide a cancer cell surface molecular recognition property that is not present in the wild-type peptide. In certain aspects, the cancer is a cancer known to have one or more tumor-associated or tumor-specific cell surface molecules (e.g., cell surface receptors, membrane proteases, and the like) and the engineered loop of the knottin peptide is engineered to bind to an extracellular domain of one or more such tumor-associated or tumor-specific cell surface molecules. By "tumor-associated cell surface molecule" is meant a cell surface molecule expressed on malignant cells with limited expression on cells of normal tissues, a cell surface molecule expressed at much higher density on malignant versus normal cells, or a cell surface molecule that is developmentally expressed.

Any tumor-associated cell surface molecule or tumor-specific cell surface molecule may be targeted by a conjugate of the present disclosure. In certain aspects, the target on the cancer cell surface to which the loop is engineered to bind is HER2, CD19, CD22, CD30, CD33, CD56, CD66/CEACAM5, CD70, CD74, CD79b, CD138, Nectin-4, Mesothelin, Transmembrane glycoprotein NMB (GPNMB), Prostate-Specific Membrane Antigen (PSMA), SLC44A4, CA6, CA-IX, $\alpha v\beta 1$ integrin, $\alpha v\beta 3$ integrin, $\alpha v\beta 5$ integrin, $\alpha v\beta 6$ integrin, $\alpha 5\beta 1$ integrin, C-X-C chemokine receptor type 4 (CXCR4), cytotoxic T-lymphocyte-associated protein 4 (CTLA-4), neuropilin-1 (NRP1), matriptase, or any other tumor-associated or tumor-specific cell surface molecules of interest.

According to certain embodiments, the target on the cancer cell surface is a receptor, e.g., a cell adhesion receptor, a receptor for a soluble factor (e.g., a growth-factor, chemokine, or other soluble factor receptor), an immune cell receptor, or the like. In certain aspects, when the receptor is a cell adhesion receptor, the receptor is an integrin. For example, a conjugate of the present disclosure may include a knottin peptide having a loop engineered to bind to any one of αvβ1 integrin, αvβ3 integrin, αvβ5 integrin, αvβ6 integrin, α5β1 integrin, or any combination thereof. According to certain embodiments, the engineered loop binds to each of αvβ1 integrin, αvβ3 integrin, αvβ5 integrin, αvβ6 integrin, and α5β1 integrin.

An EETI-based knottin peptide (designated EETI-2.5D) having an engineered binding loop that binds to each of αvβ1 integrin, αvβ3 integrin, αvβ5 integrin, αvβ6 integrin, and α5β1 integrin, which may be employed in a conjugate of the present disclosure, has the following amino acid sequence (with the integrin-binding loop underlined):

(SEQ ID NO: 6)
GCPQGRGDWAPTSCKQDSDCRAGCVCGPNGFCG

An EETI-based knottin peptide (designated EETI-2.5F) having an engineered binding loop that binds to each of αvβ1 integrin, αvβ3 integrin, αvβ5 integrin, αvβ6 integrin, and α5β1 integrin, which may be employed in a conjugate of the present disclosure, has the following amino acid sequence (with the integrin-binding loop underlined):

(SEQ ID NO: 7)
GCPRPRGDNPPLTCSQDSDCLAGCVCGPNGFCG

In some embodiments, the knottin peptide of a conjugate of the present disclosure is an integrin-binding EETI-based knottin peptide as set forth in Table 1.

TABLE 1

Example EETI Integrin-Binding Knottin Peptides

| Peptide identifier | Sequence | SEQ ID NO: |
|---|---|---|
| 1.4A | GCAEPRGDMPWTWCKQDSDCLAGCVCGPNGFCG | (SEQ ID NO: 8) |
| 1.4B | GCVGGRGDWSPKWCKQDSDCPAGCVCGPNGFCG | (SEQ ID NO: 9) |
| 1.4C | GCAELRGDRSYPECKQDSDCLAGCVCGPNGFCG | (SEQ ID NO: 10) |
| 1.4E | GCRLPRGDVPRPHCKQDSDCQAGCVCGPNGFCG | (SEQ ID NO: 11) |
| 1.4H | GCYPLRGDNPYAACKQDSDCRAGCVCGPNGFCG | (SEQ ID NO: 12) |
| 1.5B | GCTIGRGDWAPSECKQDSDCLAGCVCGPNGFCG | (SEQ ID NO: 13) |
| 1.5F | GCHPPRGDNPPVTCKQDSDCLAGCVCGPNGFCG | (SEQ ID NO: 14) |
| 2.3A | GCPEPRGDNPPPSCKQDSDCRAGCVCGPNGFCG | (SEQ ID NO: 15) |
| 2.3B | GCLPPRGDNPPPSCKQDSDCQAGCVCGPNGFCG | (SEQ ID NO: 16) |
| 2.3C | GCHLGRGDWAPVGCKQDSDCPAGCVCGPNGFCG | (SEQ ID NO: 17) |
| 2.3D | GCNVGRGDWAPSECKQDSDCPAGCVCGPNGFCG | (SEQ ID NO: 18) |
| 2.3E | GCFPGRGDWAPSSCKQDSDCRAGCVCGPNGFCG | (SEQ ID NO: 19) |

TABLE 1-continued

Example EETI Integrin-Binding Knottin Peptides

| Peptide identifier | Sequence | SEQ ID NO: |
|---|---|---|
| 2.3F | GCPLPRGDNPPTECKQDSDCQAGCVCGPNGFCG | (SEQ ID NO: 20) |
| 2.3G | GCSEARGDNPRLSCKQDSDCRAGCVCGPNGFCG | (SEQ ID NO: 21) |
| 2.3H | GCLLGRGDWAPEACKQDSDCRAGCVCGPNGFCG | (SEQ ID NO: 22) |
| 2.3I | GCHVGRGDWAPLKCKQDSDCQAGCVCGPNGFCG | (SEQ ID NO: 23) |
| 2.3J | GCVRGRGDWAPPSCKQDSDCPAGCVCGPNGFCG | (SEQ ID NO: 24) |
| 2.4A | GCLGGRGDWAPPACKQDSDCRAGCVCGPNGFCG | (SEQ ID NO: 25) |
| 2.4C | GCFVGRGDWAPLTCKQDSDCQAGCVCGPNGFCG | (SEQ ID NO: 26) |
| 2.4D | GCPVGRGDWSPASCKQDSDCRAGCVCGPNGFCG | (SEQ ID NO: 27) |
| 2.4E | GCPRPRGDNPPLTCKQDSDCLAGCVCGPNGFCG | (SEQ ID NO: 28) |
| 2.4F | GCYQGRGDWSPSSCKQDSDCPAGCVCGPNGFCG | (SEQ ID NO: 29) |
| 2.4G | GCAPGRGDWAPSECKQDSDCQAGCVCGPNGFCG | (SEQ ID NO: 30) |
| 2.4J | GCVQGRGDWSPPSCKQDSDCPAGCVCGPNGFCG | (SEQ ID NO: 31) |
| 2.5A | GCHVGRGDWAPEECKQDSDCQAGCVCGPNGFCG | (SEQ ID NO: 32) |
| 2.5C | GCDGGRGDWAPPACKQDSDCRAGCVCGPNGFCG | (SEQ ID NO: 33) |
| 2.5D | GCPQGRGDWAPTSCKQDSDCRAGCVCGPNGFCG | (SEQ ID NO: 6) |
| 2.5F | GCPRPRGDNPPLTCKQDSDCLAGCVCGPNGFCG | (SEQ ID NO: 7) |
| 2.5H | GCPQGRGDWAPEWCKQDSDCPAGCVCGPNGFCG | (SEQ ID NO: 34) |
| 2.5J | GCPRGRGDWSPPACKQDSDCQAGCVCGPNGFCG | (SEQ ID NO: 35) |

In some embodiments, the knottin peptide of a conjugate of the present disclosure is an integrin-binding AgRP-based knottin peptide as set forth in Table 2.

TABLE 2

Example AgRP Integrin-Binding Knottin Peptides

| Clone | Loop 4 sequence |
|---|---|
| 7A (5E) (SEQ ID NO: 36) | GCVRLHESCLGQQVPCCDPAATCYCSGRGDNDLVCYCR |
| 7B (SEQ ID NO: 37) | GCVRLHESCLGQQVPCCDPAATCYCKGRGDARLQCYCR |
| 7E (SEQ ID NO: 38) | GCVRLHESCLGQQVPCCDPAATCYCVGRGDDNLKCYCR |
| 7J (6B) (SEQ ID NO: 39) | GCVRLHESCLGQQVPCCDPAATCYCEGRGDRDMKCYCR |
| 7C (SEQ ID NO: 40) | GCVRLHESCLGQQVPCCDPAATCYC YGRGDNDLR CYCR |

In certain aspects, the knottin peptide includes one or more unnatural amino acids. Unnatural amino acids which find use for preparing the conjugates of the present disclosure include those having a functional group selected from an azide, alkyne, alkene, amino-oxy, hydrazine, aldehyde, nitrone, nitrile oxide, cyclopropene, norbornene, iso-cyanide, aryl halide, and boronic acid functional group. Unnatural amino acids which may be incorporated into a knottin peptide of a knottin-drug conjugate of the present disclosure, which unnatural amino acid may be selected to provide a functional group of interest are known and described in, e.g., Maza et al. (2015) *Bioconjug. Chem.* 26(9):1884-9; Patterson et al. (2014) *ACS Chem. Biol.* 9:592-605; Adumeau et al. (2016) *Mol. Imaging Biol.* (2):153-65; and elsewhere.

As one example, the EETI-2.5F peptide provided above may be modified to include an unnatural amino acid, e.g., having a functional group useful for attachment to a linker, e.g., a linker attached to a nucleoside drug. According to one embodiment, the unnatural amino acid replaces the serine at position 15 of EETI-2.5F (bold in the above EETI-2.5F sequence) as provided in the following amino acid sequence, where Z (bold and underlined) represents an unnatural amino acid:

(SEQ ID NO: 41)
GCPRPRGDNPPLTCZQDSDCLAGCVCGPNGFCG

In certain aspects, a knottin peptide of a conjugate of the present disclosure, including but not limited to the modified EETI-2.5F peptide above, includes an unnatural amino acid that includes an azide functional group. An example of such an unnatural amino acid is 5-azido-L-norvaline. As demonstrated in the Experimental section below, an EETI-2.5F peptide that includes 5-azido-L-norvaline at position 15 finds use for attaching to various linkers, which were in turn attached to a nucleoside drug (gemcitabine). The resulting KDC selectively delivered the nucleoside drug to a variety of malignant cell lines expressing tumor-associated integrin receptors. This KDC is capable of binding to integrins expressed on malignant cells with low-nanomolar affinity, is internalized via an integrin-mediated process, releases the nucleoside drug upon internalization, and is a highly potent inhibitor of brain, breast, ovarian, and pancreatic cancer cells. In some embodiments, 2.5F-gemcitabine has been shown to kill cancer cell lines in culture, including for example diffuse intrinsic pontine glioma (DIPG).

The manner in which the knottin peptide having an engineered loop that binds to a target on a cancer cell surface is developed may vary. Rational and combinatorial approaches have been used to engineer knottins with novel molecular recognition properties. For example, a library of knottin proteins may be created and screened, e.g., by bacterial display, phage display, yeast surface display, fluorescence-activated cell sorting (FACS), and/or any other suitable screening method.

Yeast surface display is a powerful combinatorial technology that has been used to engineer proteins with novel molecular recognition properties, increased target binding affinity, proper folding, and improved stability. In this platform, libraries of protein variants are generated and screened in a high-throughput manner to isolate mutants with desired biochemical and biophysical properties. Yeast surface display has proven to be a successful combinatorial method for engineering knottins with altered molecular recognition. Yeast surface display benefits from quality control mechanisms of the eukaryotic secretory pathway, chaperone-assisted folding, and efficient disulfide bond formation.

One example approach for developing a knottin peptide having an engineered loop that binds to a target of interest on a cancer cell involves genetically fusing the peptide to the yeast mating agglutinin protein Aga2p, which is attached by two disulfide binds to the yeast cell wall protein Aga1p. This Aga2p-fusion construct, and a chromosomally integrated Aga1p expression cassette, may be expressed under the control of a suitable promoter, such as a galactose-inducible promoter. N- or C-terminal epitope tags may be included to measure cell surface expression levels by flow cytometry using fluorescently labeled primary or secondary antibodies. This construct represents the most widely used display format, where the N-terminus of the knottin (or other protein to be engineered) is fused to Aga2, but several alternative variations of the yeast surface display plasmid have been described and may be employed to develop a knottin peptide for use in a conjugate of the present disclosure. One of the benefits of this screening platform over panning-based methods used with phage or mRNA display is that two-color FACS can be used to quantitatively discriminate clones that differ by as little as two-fold in binding affinity to the desired target.

To selectively mutate knottin loop regions at the DNA level, degenerate codons can be introduced by oligonucleotide assembly using, e.g., overlap extension PCR. Next, the genetic material may be amplified using flanking primers with sufficient overlap with the yeast display vector for homologous recombination in yeast. This assembly and amplification method allow knottin libraries to be created at relatively low cost and effort. Synthetic oligonucleotide libraries and recent methods have been developed that allow defined control over library composition.

In certain aspects, a display library (e.g., a yeast display library) is screened for binding to the target of interest on a cancer cell by FACS. When screening knottin libraries by FACS, an enriched pool of binders generally emerges in 4-7 rounds of sorting. Two-color FACS may be used for library screening, where one fluorescent label can be used to detect the c-myc epitope tag and the other to measure interaction of the knottin mutant against the binding target of interest. Different instrument lasers and/or filter sets can be used to measure excitation and emission properties of the two fluorophores at single-cell resolution. This enables yeast expression levels to be normalized with binding. That is, a knottin that exhibits poor yeast expression but binds a high amount of a target can be distinguished from a knottin that is expressed at high levels but binds weakly to a target. Accordingly, a two-dimensional flow cytometry plot of expression versus binding will result in a diagonal population of yeast cells that bind to target antigen. High-affinity binders can be isolated using library sort gates. Alternatively, in an initial sort round it could be useful to clear the library of undesired clones that do not express full-length.

The target used in the screening is structurally and functionally relevant for the final application, e.g., mimics the target of interest on the surface of the cancer cells of interest. In certain aspects, the target used in the screening is HER2, CD19, CD22, CD30, CD33, CD56, CD66/CEACAM5, CD70, CD74, CD79b, CD138, Nectin-4, Mesothelin, Transmembrane glycoprotein NMB (GPNMB), Prostate-Specific Membrane Antigen (PSMA), SLC44A4, CA6, CA-IX, $\alpha v\beta 1$ integrin, $\alpha v\beta 3$ integrin, $\alpha v\beta 5$ integrin, $\alpha v\beta 6$ integrin, $\alpha 5\beta 1$ integrin, C-X-C chemokine receptor type 4 (CXCR4), cytotoxic T-lymphocyte-associated protein 4 (CTLA-4), neuropilin-1 (NRP1), matriptase, or any other tumor-associated or tumor-specific cell surface molecules of interest.

Following enrichment of knottin libraries for binders against the cancer cell surface target of interest, the yeast plasmids are recovered and sequenced. Additional rounds of FACS can be performed under increased sorting stringency. The binding affinities or kinetic off-rates of individual yeast-displayed knottin clones may then be measured.

Once knottin peptides having an engineered loop that binds to the cancer cell surface target of interest have been identified by surface display (e.g., yeast surface display), the engineered knottins may be produced using a suitable method. The small size of knottins makes them amenable to production by both chemical synthesis and recombinant expression. According to certain embodiments, the knottin peptide may be produced by solid phase peptide synthesis followed by in vitro folding. Chemical synthesis permits facile incorporation of unnatural amino acids or other chemical handles into knottin peptides.

Knottin peptide sequences are readily synthesized using solid phase peptide chemistry on an automated synthesizer. For example, standard 9-fluorenylmethyloxycarbonyl (Fmoc)-based solid phase peptide chemistry may be employed. The linear peptide may then be folded under conditions that promote oxidation of cysteine side chain thiols to form disulfide bonds, followed by purification, e.g., by reversed-phase high-performance liquid chromatography (RP-HPLC).

In certain aspects, the knottin protein is produced using a recombinant DNA approach. Strategies have been developed for producing knottins using recombinant methods in a variety of host cell types. For example, functional knottins have been produced with barnase as a genetic fusion partner, which promotes folding in the *E. coli* periplasmic space and serves as a useful purification handle. According to certain embodiments, the engineered knottin peptide is expressed in yeast. The yeast strain *Pichia pastoris*, for example, has been successfully employed to produce 2-10 mg/L of purified engineered knottins. The yeast expression construct may encode one or more tags (e.g., a C-terminal hexahistadine tag for purification by, e.g., metal chelating chromatography (Ni-NTA)). Size exclusion chromatography may then be used to remove aggregates, misfolded multimers, and the like.

Aspects of the present disclosure include nucleic acids that encode the knottin peptides employed in the conjugates of the present disclosure. That is, provided are nucleic acids that encode any of the subject knottin peptides described herein having an engineered loop that binds to a target of interest on a cancer cell surface. In certain aspects, such a nucleic acid is present in an expression vector. The expression vector includes a promoter operably linked to the nucleic acid encoding the knottin peptide, the promoter being selected based on the type of host cell selected to express the knottin peptide. Also provided are host cells that include any of the knottin peptide-encoding nucleic acids of the present disclosure, as well as any expression vectors including the same.

Methods are available for measuring the affinity of knottins for receptors expressed on the surface of cells (e.g., cancer cells, such as mammalian cancer cells) using direct binding or competition binding assays. In a direct binding assay, an equilibrium binding constant ($K_D$) may be measured using a knottin conjugated to a fluorophore or radioisotope, or a knottin that contains an N- or C-terminal epitope tag for detection by a labeled antibody. If labels or tags are not feasible or desired, a competition binding assay can be used to determine the half-maximal inhibitory concentration ($IC_{50}$), the amount of unlabeled knottin at which 50% of the maximal signal of the labeled competitor is detectable. A $K_D$ value can then be calculated from the measured $IC_{50}$ value. Ligand depletion will be more pronounced when measuring high-affinity interactions over a lower concentration range, and can be avoided or minimized by decreasing the number of cells added in the experiment or by increasing the binding reaction volumes.

In certain aspects, the knottin peptide has an equilibrium binding constant ($K_D$) for the cell-surface molecule of from about 0.01 nM to 100 nM, such as from about 0.025 nM to 75 nM, about 0.05 nM to 50 nm, about 0.075 nM to 25 nM, or from about 0.1 nM to 10 nM. In some embodiments, the knottin peptide has an equilibrium binding constant ($K_D$) for the cell-surface molecule of from about 0.1 nM to 10 nM. In some embodiments, the knottin peptide has an equilibrium binding constant ($K_D$) for the cell-surface molecule of about 0.1 nM. In some embodiments, the knottin peptide has an equilibrium binding constant ($K_D$) for the cell-surface molecule of about 0.5 nM. In some embodiments, the knottin peptide has an equilibrium binding constant ($K_D$) for the cell-surface molecule of about 1 nM. In some embodiments, the knottin peptide has an equilibrium binding constant ($K_D$) for the cell-surface molecule of about 5 nM. In some embodiments, the knottin peptide has an equilibrium binding constant ($K_D$) for the cell-surface molecule of about 10 nM.

Detailed guidance and specific protocols for engineering knottins by yeast surface display technology, including knottin library construction and screening, as well as knottin production by chemical synthesis and recombinant expression, and further for cell binding assays to measure the affinity of knottins to molecules (e.g., receptors) expressed on the surface of cells using direct binding or competition binding assays, are described in Moore, S. and Cochran, J. (2012) Engineering Knottins as Novel Binding Agents, *Methods in Enzymology*, 503, 223-251.

Drugs, Linkers, and Methods of Making Knottin-Drug Conjugates

As summarized above, a knottin-drug conjugate (KDC) of the present disclosure includes a drug (e.g., a nucleoside drug) conjugated to the knottin peptide through a linker. Example drugs and linkers that may be employed in the KDCs of the present disclosure, as well as example approaches for conjugating the drugs/linkers to the knottin peptides, will now be described.

In certain aspects, the drug is a nucleoside drug. A "nucleoside" includes (e.g., consists of) a nucleobase (such as a purine or pyrimidine) bound covalently to a pentose monosaccharide, e.g., a 5-carbon sugar such as ribose. By "nucleoside analogue" is meant a nucleoside in which either the nucleobase and/or the pentose monosaccharide are unnatural. As used herein, a "nucleoside drug" includes (e.g., consists of) a nucleoside analogue that causes a physiological change within the body of an individual. In certain aspects, the nucleoside analogue is any one of an adenoside/deoxyadenosine analogue, cytidine/deoxycytidine, guanosine/deoxyguanosine analogue, thymidine/deoxythymidine analogue, or a deoxyuridine analogue. In some embodiments, the nucleoside analogue may be any one of gemcitabine, cytarabine, troxacitabine, decitabine, cladribine, fludarabine, clofarabine, or 2'-C-cyano-2'-deoxy-1-3-D-arabino-pentofuranosylcytosine (CNDAC). According to one embodiment, the nucleoside analogue is gemcitabine. In certain aspects, the nucleoside analogue is cytarabine.

According to certain embodiments, the drug is a nucleotide drug. A "nucleotide" is a nucleoside with one to three phosphate groups attached thereto. A "nucleotide analog" is a nucleotide in which either the nucleobase and/or the pentose monosaccharide (e.g., a 5-carbon sugar such as ribose) are unnatural. A "nucleotide drug" includes (e.g., consists of) a nucleotide analogue that causes a physiological change within the body of an individual.

Linkers that find use in the conjugates of the present disclosure include ester linkers, amide linkers, maleimide or maleimide-based linkers; valine-citrulline linkers; hydrazone linkers; N-succinimidyl-4-(2-pyridyldithio)butyrate (SPDB) linkers; Succinimidyl-4-(N-maleimidomethyl)cyclohexane-1-carboxylate (SMCC) linkers; vinylsulfone-based linkers; linkers that include polyethylene glycol (PEG), such as, but not limited to tetraethylene glycol; linkers that include propanoic acid; linkers that include caproleic acid, and linkers including any combination thereof.

In certain aspects, the linker is a chemically-labile linker, such as an acid-cleavable linker that is stable at neutral pH (bloodstream pH 7.3-7.5) but undergoes hydrolysis upon internalization into the mildly acidic endosomes (pH 5.0-6.5) and lysosomes (pH 4.5-5.0) of a target cell (e.g., a cancer cell). Chemically-labile linkers include, but are not limited to, hydrazone-based linkers, oxime-based linkers, carbonate-based linkers, ester-based linkers, etc. According to certain embodiments, the linker is an enzyme-labile linker, such as an enzyme-labile linker that is stable in the bloodstream but undergoes enzymatic cleavage upon internalization into a target cell, e.g., by a lysosomal protease (such as cathepsin or plasmin) in a lysosome of the target cell (e.g., a cancer cell). Enzyme-labile linkers include, but are not limited to, linkers that include peptidic bonds, e.g., dipeptide-based linkers such as valine-citrulline linkers, such as a maleimidocaproyl-valine-citruline-p-aminobenzyl (MC-vc-PAB) linker, a valyl-alanyl-para-aminobenzyloxy (Val-Ala-PAB) linker, and the like. Chemically-labile linkers, enzyme-labile, and non-cleavable linkers are known and described in detail, e.g., in Ducry & Stump (2010) Bioconjugate Chem. 21:5-13.

Numerous strategies are available for linking the drug (e.g., a nucleoside drug) to the knottin peptide through a linker. For example, a nucleoside drug may be derivatized by covalently attaching the linker to the drug, where the linker has a functional group capable of reacting with a "chemical handle" on the knottin peptide. The functional group on the linker may vary and may be selected based on compatibility with the chemical handle on the knottin peptide. According to one embodiment, the chemical handle on the knottin peptide is provided by incorporation of an unnatural amino acid having the chemical handle into the knottin peptide. Knottin peptides that include such an unnatural amino acid are described above, and may be incorporated via chemical synthesis or recombinant approaches (e.g., using a suitable orthogonal amino acyl tRNA synthetase-tRNA pair for incorporation of the unnatural amino acid during translation in a host cell).

In other aspects, the chemical handle on the knottin peptide is provided using an approach that does not involve an unnatural amino acid. A knottin peptide containing no unnatural amino acids could be conjugated to a nucleoside drug or drug-linker construct by utilizing, e.g., nucleophilic functional groups of the knottin (such as the N-terminal amine or the primary amine of lysine, or any other nucleophilic amino acid residue) as a nucleophile in a substitution reaction with a drug/linker construct bearing a reactive leaving group or other electrophilic group. An example would be to prepare a drug-linker construct bearing an N-hydroxysuccinimidyl (NHS) ester and allow it to react with the peptide under aqueous conditions at elevated pH (~10) or in polar organic solvents such as DMSO with an added non-nucleophilic base, such as N,N-diisopropylethylamine. In the case of EETI 2.5F, the N-terminus is the most reactive site as the peptide does not contain any lysines or reduced disulfides (cysteine) residues capable of reacting with an NHS ester.

Figure 3:
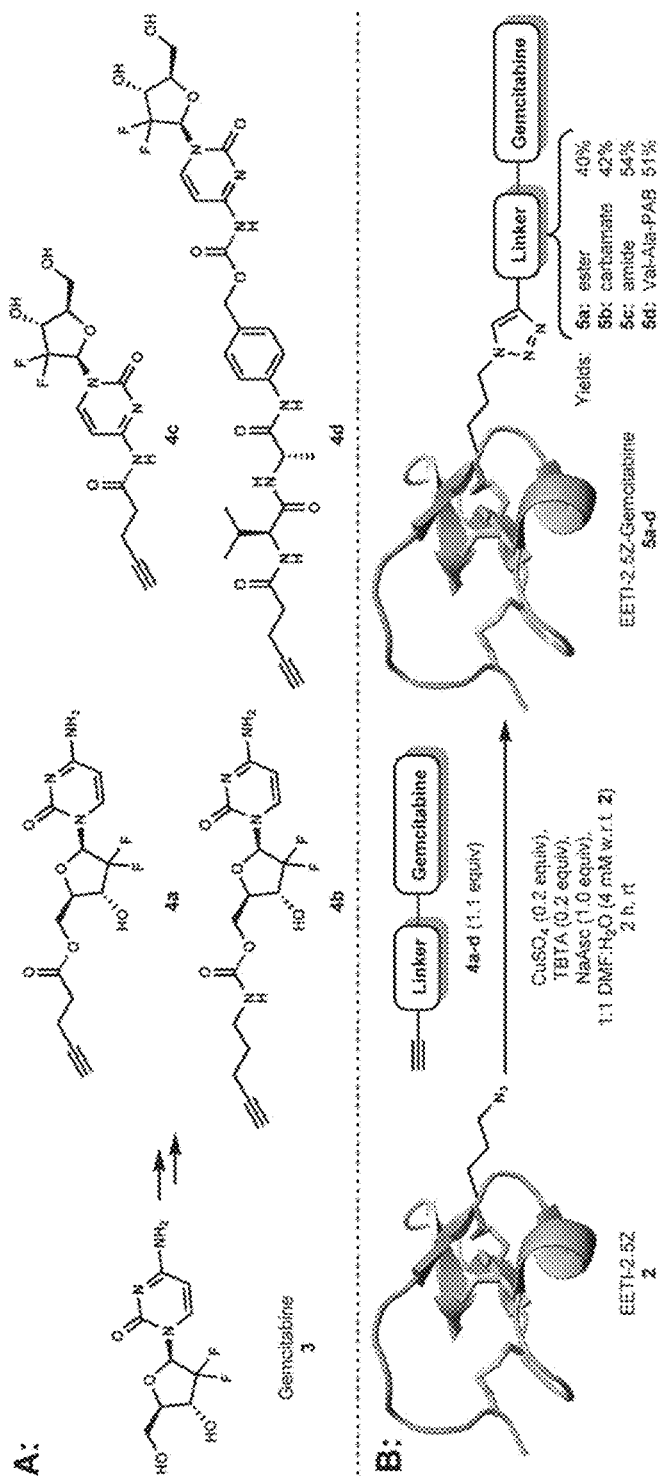
FIG. 3 shows a scheme for producing knottin-drug conjugates according to one embodiment of the present disclosure.

The functional group of an unnatural amino acid present in the knottin peptide may be an azide, alkyne, alkene, amino-oxy, hydrazine, aldehyde, asaldehyde, nitrone, nitrile oxide, cyclopropene, norbornene, iso-cyanide, aryl halide, boronic acid, diazo, tetrazine, tetrazole, quadrocyclane, iodobenzene, or other suitable functional group, and the functional group on the linker is selected to react with the functional group of the unnatural amino acid (or vice versa). As just one example, an azide-bearing unnatural amino acid (e.g., 5-azido-L-norvaline, or the like) may be incorporated into the knottin peptide and the linker portion of the linker-drug moiety may include an alkyne functional group, such that the knottin peptide and linker-drug moiety are covalently conjugated via azide-alkyne cycloaddition. Examples of this particular embodiment are described in the Experimental section below. Briefly, the nucleoside analogue (gemcitabine) was derivatized with an ester, carbamate, amide, or Val-Ala-PAB linker having an alkyne functional group as schematically illustrated in FIG. 3, Panel A. Conjugation was carried out using a copper-catalyzed azide-alkyne cycloaddition reaction according to the scheme schematically illustrated in FIG. 3, Panel B.

Accordingly, aspects of the present disclosure include methods of making a knottin-drug conjugate. The methods include conjugating a drug (e.g., a nucleoside drug) to a knottin peptide that includes an engineered loop that binds to a target on a cancer cell surface. The knottin peptide and drug may be any of the peptides and drugs described herein.

According to certain embodiments, the methods include derivatizing the nucleoside drug by attaching a linker to the drug, and then attaching the linker to the knottin peptide. Attachment of the linker to the knottin peptide, in certain aspects, includes reacting a functional group of the linker with a functional group of an unnatural amino acid present in the knottin peptide. In one particular embodiment, the functional group of the linker is a terminal alkyne and the functional group of the unnatural amino acid present in the knottin peptide is an azide, and attachment of the linker to the knottin peptide is by azide-alkyne cycloaddition to form a triazole from the terminal alkyne of the linker and the azide of the unnatural amino acid. In certain aspects, the linker is attached to the knottin peptide prior to being attached to the nucleoside drug.

It will be appreciated that the particular approach for attaching the linker to the drug and the linker to the knottin peptide will vary depending upon the particular drug and functional groups selected and employed in the linker and knottin peptide.

In some embodiments, the knottin-drug conjugate includes a knottin peptide having an engineered loop that binds to an integrin, e.g., present on a cancer cell surface. In certain aspects, the integrin is any one of, or any combination of, $\alpha v \beta 1$ integrin, $\alpha v \beta 3$ integrin, $\alpha v \beta 5$ integrin, $\alpha v \beta 6$ integrin, and $\alpha 5 \beta 1$ integrin.

In certain aspects, the nucleoside drug is a nucleoside analogue. Such a nucleoside analogue may be, e.g., Gemcitabine.

According to certain embodiments, the linker is a cleavable linker. Such a cleavable linker may be a dipeptide-based cleavable linker. In certain aspects, the dipeptide-based cleavable linker is a Val-Ala-PAB linker.

According to one embodiment of the present disclosure, the knottin-drug conjugate includes a knottin peptide having an engineered loop that binds to an integrin (e.g., $\alpha v \beta 1$ integrin, $\alpha v \beta 3$ integrin, $\alpha v \beta 5$ integrin, $\alpha v \beta 6$ integrin, $\alpha 5 \beta 1$ integrin, and any combination thereof) on a cancer cell surface (e.g., an EETI-2.5F-based knottin peptide (e.g., an EETI-2.5Z-based peptide)) conjugated to a nucleoside drug (e.g., a nucleoside analogue such as, for example, Gemcitabine) via a cleavable linker, e.g., a dipeptide-based cleavable linker such as, for example, a Val-Ala-PAB linker.

Compositions

Also provided are compositions that include a knottin-drug conjugate of the present disclosure. The compositions may include any of the knottin-drug conjugates described herein.

In certain aspects, the compositions include a conjugate of the present disclosure present in a liquid medium. The liquid medium may be an aqueous liquid medium, such as water, a buffered solution, and the like. One or more additives such as a salt (e.g., NaCl, MgCl$_2$, KCl, MgSO$_4$), a buffering agent (a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), N-tris[Hydroxymethyl]methyl-3-aminopropanesulfonic acid (TAPS), etc.), a protease inhibitor, glycerol, and the like may be present in such compositions.

Pharmaceutical compositions are also provided. The pharmaceutical compositions include any of the knottin-drug conjugates of the present disclosure, and a pharmaceutically-acceptable excipient. The pharmaceutical compositions generally include a therapeutically effective amount of the conjugate. By "therapeutically effective amount" is meant a dosage sufficient to produce a desired result, e.g., an amount sufficient to effect beneficial or desired therapeutic (including preventative) results, such as a reduction in a symptom of cancer, e.g., a cancer in which a target on the surface of cells of the cancer is bound by the engineered loop of the knottin peptide of the conjugate present in the composition.

A conjugate of the present disclosure can be incorporated into a variety of formulations for therapeutic administration. More particularly, the conjugate can be formulated into pharmaceutical compositions by combination with appropriate pharmaceutically acceptable excipients or diluents, and may be formulated into preparations in solid, semi-solid, liquid or gaseous forms, such as tablets, capsules, powders, granules, ointments, solutions, injections, inhalants and aerosols.

Formulations of the conjugates of the present disclosure suitable for administration to an individual (e.g., suitable for human administration) are generally sterile and may further be free of detectable pyrogens or other contaminants contraindicated for administration to an individual according to a selected route of administration.

In pharmaceutical dosage forms, the conjugates can be administered alone or in appropriate association, as well as in combination, with other pharmaceutically active compounds. The following methods and excipients are merely examples and are in no way limiting.

For oral preparations, the conjugates can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The conjugates can be formulated into preparations for injection by dissolving, suspending or emulsifying them in an aqueous or non-aqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The pharmaceutical composition may be in a liquid form, a lyophilized form or a liquid form reconstituted from a lyophilized form, where the lyophilized preparation is to be reconstituted with a sterile solution prior to administration. The standard procedure for reconstituting a lyophilized composition is to add back a volume of pure water (typically equivalent to the volume removed during lyophilization); however solutions comprising antibacterial agents may be used for the production of pharmaceutical compositions for parenteral administration.

An aqueous formulation of the conjugate may be prepared in a pH-buffered solution, e.g., at pH ranging from about 4.0 to about 7.0, or from about 5.0 to about 6.0, or alternatively about 5.5. Examples of buffers that are suitable for a pH within this range include phosphate-, histidine-, citrate-, succinate-, acetate-buffers and other organic acid buffers. The buffer concentration can be from about 1 mM to about 100 mM, or from about 5 mM to about 50 mM, depending, e.g., on the buffer and the desired tonicity of the formulation.

Methods of Use

Also provided are methods of using the knottin-drug conjugates of the present disclosure. According to certain embodiments, provided are methods of treating a subject having cancer. Such methods may include administering to a subject having cancer a therapeutically effective amount of any of the knottin-drug conjugates or pharmaceutical compositions described elsewhere herein, where the engineered loop of the knottin peptide binds to a cell surface target associated with or specific to the cancer.

The conjugate may be administered alone (e.g., in monotherapy) or in combination (e.g., in combination therapy) with one or more additional therapeutic agents.

In some embodiments, an effective amount of the conjugate is an amount that, when administered alone (e.g., in monotherapy) or in combination (e.g., in combination therapy) with one or more additional therapeutic agents, in one or more doses, is effective to reduce the symptoms of cancer in the individual by at least about 5%, at least about 10%, at least about 15%, at least about 20%, at least about 25%, at least about 30%, at least about 40%, at least about 50%, at least about 60%, at least about 70%, at least about 80%, at least about 90%, or more, compared to the symptoms in the individual in the absence of treatment with the conjugate.

In certain aspects, the methods of treating cancer (that is, treating an individual having cancer) inhibit growth, metastasis and/or invasiveness of cancer cells in the individual when the conjugate is administered in an effective amount.

Cancers which may be treated using the methods of the present disclosure include, but are not limited to, solid tumors, brain cancer, breast cancer, lung cancer (e.g., non-small cell lung cancer), ovarian cancer, prostate cancer, pancreatic cancer (e.g., adenocarcinoma of the pancreas), diffuse intrinsic pontine glioma (DIPG), colorectal carcinoma, renal cell carcinoma, Hodgkin's lymphoma, Non-Hodgkin's lymphoma, anaplastic large cell lymphoma, acute myelogenous leukemia, multiple myeloma, and any other type of cancer which may be treated using a conjugate-based therapy.

The conjugates of the present disclosure are administered to an individual using any available method and route suitable for drug delivery, including in vivo and ex vivo methods, as well as systemic and localized routes of administration. Conventional and pharmaceutically acceptable routes of administration include intranasal, intramuscular, intra-tracheal, subcutaneous, intradermal, topical application, ocular, intravenous, intra-arterial, nasal, oral, and other enteral and parenteral routes of administration. Routes of administration may be combined, if desired, or adjusted depending upon the conjugate and/or the desired effect. The conjugates may be administered in a single dose or in multiple doses. In some embodiments, the conjugate is administered intravenously. In some embodiments, the conjugate is administered by injection, e.g., for systemic delivery (e.g., intravenous infusion) or to a local site.

A variety of individuals are treatable according to the subject methods. Generally such subjects are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In some embodiments, the individual will be human.

By treatment is meant at least an amelioration of the symptoms associated with the cancer of the individual, where amelioration is used in a broad sense to refer to at least a reduction in the magnitude of a parameter, e.g. symptom, associated with the cancer being treated. As such, treatment also includes situations where the cancer, or at least symptoms associated therewith, are completely inhibited, e.g. prevented from happening, or stopped, e.g. terminated, such that the individual no longer suffers from the cancer, or at least the symptoms that characterize the cancer.

Dosing is dependent on severity and responsiveness of the disease state to be treated. Optimal dosing schedules can be calculated from measurements of drug accumulation in the body of the patient. The administering physician can determine optimum dosages, dosing methodologies and repetition rates. Optimum dosages may vary depending on the relative potency of individual conjugates, and can generally be estimated based on $EC_{50}$s found to be effective in in vitro and in vivo animal models, etc. In general, dosage is from about 0.01 μg to about 100 g per kg of body weight, and may be given once or more daily, weekly, monthly or yearly. In certain aspects, the dosage is from about 1 μg/kg to 100 mg/kg or more, depending on the factors mentioned above. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, where the conjugate is administered in maintenance doses, ranging from about 0.01 μg to about 100 g per kg of body weight, once or more daily, to once every several months, once every six months, once every year, or at any other suitable frequency.

The therapeutic methods of the present disclosure may include administering a single type of conjugate to a subject, or may include administering two or more types of conjugates to a subject by administration of a cocktail of different conjugates, where the engineered loops of the two or more types of conjugates are engineered to bind to distinct cancer cell surface targets or different regions of a single cancer cell surface target.

Kits

As summarized above, the present disclosure provides kits. According to certain embodiments, the kits include a therapeutically effective amount of any of the knottin-drug conjugates described herein, or any of the pharmaceutical compositions described herein, and instructions for administering the pharmaceutical composition to a subject in need thereof. In certain aspects, the kits include a pharmaceutical composition of the present disclosure, present in a container. The container may be a tube, vial, or the like. According to certain embodiments, kit includes the pharmaceutical composition present in one or more unit dosages, such as 1, 2 or more, 3 or more, 4 or more, 5 or more, etc. unit dosages.

Components of the kits may be present in separate containers, or multiple components may be present in a single container.

The instructions for administering the pharmaceutical composition to a subject may be recorded on a suitable recording medium. For example, the instructions may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., portable flash drive, DVD, CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, the means for obtaining the instructions is recorded on a suitable substrate.

The following examples are offered by way of illustration and not by way of limitation.

EXPERIMENTAL

Materials and Methods 1.1. Methods for Chemical Synthesis

All reactions were performed in a fume hood under a nitrogen atmosphere, using oven-dried glassware unless otherwise indicated. Flash column chromatography was performed on a Teledyne Isco purification system using silica gel flash cartridges (SiliCycle®, SiliaSep™ 40-63 μm, 60 Å). HPLC was performed on an Agilent 1260 Infinity preparative scale purification system using a Grace Vydac C4 reverse-phase column (21.2×250 mm) and an Agilent PrepHT Zorbax Eclipse XDB-C18 reverse-phase column (21.2×250 mm). $^1$H and $^{13}$C NMR spectra were recorded on a Bruker AV-500 spectrometer. $^1$H NMR chemical shifts (δ) are reported in parts per million (ppm) and are referenced relative to residual $CD_3OH$ (δ 4.87) or $(CD_3)(CD_2H)SO$ (δ 2.50). $^{13}$C chemical shifts are reported in parts per million downfield of TMS and are referenced to the carbon resonance of $CD_3OD$ (δ 49.0) or $(CD_3)_2SO$ (δ 39.5). Data are represented as follows: chemical shift, multiplicity (s=singlet, d=doublet, t=triplet, q=quartet, m=multiplet, brs=broad singlet), integration, and coupling constants in Hertz (Hz). Low-resolution mass spectra (ESI-MS) were collected on a Shimadzu 20-20 ESI LCMS instrument. High-resolution mass spectra (Q-TOF) were collected on an Agilent 1260 HPLC-MS/Bruker micrOTOF-Q II hybrid quadrupole-time of flight HPLC-HRMS instrument. The column used was an Agilent Zorbax SB300 C8 reverse-phase column (100×2.1 mm) at 40° C. with 0.3 mL/min flow rate using dilute aqueous TFA (Solvent A=0.05% TFA, 99.95% water v/v) and TFA/MeCN (Solvent B=0.05% TFA, 99.95% MeCN v/v) as eluents. The solvent gradient increased from 0% Solvent B to 95% Solvent B over 15 min and held at 95% Solvent B for 1 min. Data was collected in full scan MS mode with a mass range of 400-4000 Da and collision RF setting of 800 Vpp.

1.2. Materials for Chemical Synthesis

Ultrapure water used in manipulations of peptides was purified using an EMD Millipore MilliQ water purification system. Dry THF, DCM, and DMF were purchased from Acros Organics and stored under a nitrogen atmosphere. Deuterated solvents were purchased from Cambridge Isotope Laboratories, Inc. and used as received. Fmoc-5-azido-L-norvaline was purchased from Chem-Impex International, Inc. All other amino acids and HOBt were purchased from CSBio. All other commercially available reagents were purchased from AK Scientific, Inc., ApexBio, Fisher Scientific, GFS Chemicals, Inc., Oakwood Products, Inc., Sigma-Aldrich Co., and Tokyo Chemical Industry Co., Ltd. and were used as received.

1.3. Methods for Cell Culture

U87MG, and PANC-1 cells were grown in Dulbecco's Modified Eagle Medium (DMEM) with 10% fetal bovine serum (FBS) and 1% penicillin/streptomycin. MDA-MB-468 cells were grown in DMEM and Ham's F-12 medium (DMEM/F12) with 10% FBS and 1% penicillin/streptomycin. A2780 and BxPC3 cells were grown in Roswell Park Memorial Institute medium (RPMI) 1640+L-glutamine, with 10% FBS and 1% penicillin/streptomycin. D270 cells were grown in MEM (Richter's modification, no phenol red) with 10% FBS and 0.1% Gentamicin. Unless otherwise specified, cells were incubated at 37° C., 5% $CO_2$. Flow cytometry was performed using an EMD Millipore Guava EasyCyte 8HT flow cytometer and the resulting data were evaluated using FlowJo software provided by TreeStar, Inc. Cell proliferation was measured using the Dojindo Cell Counting Kit-8 by replacing the media in each well with 100 μL of media containing 10% WST-8. After incubation for 1 h at 37° C., absorbance, A, at 450 nm was measured with a BioTek Synergy H4 microtiter plate reader. The background signal of CCK-8 alone was subtracted from all samples. Cell proliferation was then expressed as a percentage of absorbance relative to the control of untreated cells (Equation 2). Nonlinear regression analysis was performed using Graph-Pad Prism.

Relative Proliferation $$\text{Relative Proliferation} = \frac{A_{treatment} - A_{background}}{A_{untreated} - A_{background}} \times 100\%. \quad \text{Equation 1}$$

1.4. Materials for Cell Culture

U87MG, and MDA-MB-468 cell lines were obtained from American Type Culture Collection (ATCC), and A2780 cells were obtained from Sigma-Aldrich. D270 cells were obtained from the laboratory of Dr. Gerald Grant (Stanford University School of Medicine—Neurosurgery). BxPC3 cells were obtained from the laboratory of Dr. Anson Lowe (Stanford University School of Medicine—Gastroenterology & Hepatology). PANC-1 cells were obtained from the laboratory of Dr. Albert Koong (Stanford University School of Medicine—Radiation Therapy). Cell lines obtained from ATCC were tested by the manufacturer for sterility (aerobic and anaerobic cultures), human pathogens (HIV, HepB, HPV, EBV, *mycoplasma* and CMV) and authenticity (cytochrome C oxidase I (COI) and short tandem repeat (STR) analysis) as per manufacturer's certificate of analysis. A2780 cells, obtained from Sigma-Aldrich, were tested by the Culture Collections division of Public Health England for sterility (aerobic and anaerobic cultures), human pathogens (*mycoplasma*) and authenticity (mitochondrial DNA sequencing and STR analysis). 0.05% Trypsin-EDTA (phenol red), DMEM, FBS, 1% penicillin/streptomycin, DMEM/F12, RPMI 1640, MEM (Richter's modification, no phenol red), and 0.1% Gentamicin were purchased from Gibco. All other media components were purchased from Life Technologies and used as received. The Cell Counting Kit-8 (CCK-8) kit was purchased from Dojindo Molecular Technologies, Inc. Trypan Blue, 0.4% was purchased from Invitrogen.

Example 1—Preparation of a Knottin Peptide Including an Azide-Containing Unnatural Amino Acid In previous work, it was shown that when labeled with fluorescent small molecules, radioisotopes, or ultrasound contrast reagents, the EETI-2.5F knottin peptide can be used for in vivo imaging of tumors in mice, including intracranial patient derived xenografts. Given the high tumor imaging contrast observed in these studies with low levels of probe accumulation in non-target organs including liver and kidney, we reasoned that the tumor targeting properties of EETI-2.5F might be leveraged to deliver a drug payload selectively to tumors—a desirable goal as evidenced by significant investment in the development of antibody-drug conjugates (ADCs).

Described in this example are knottin peptide-drug conjugates, synthesized using a variety of drug-linker strategies, and highlight a conjugate as a potent inhibitor of tumor cell growth in vitro against a variety of malignant cell lines. Also provided is evidence that integrin-binding is essential for potency, the mechanism of internalization is integrin-mediated, and the drug payload is released intracellularly.

As shown in FIG. 2, it was hypothesized that a variant of knottin EETI 2.5F containing an azide-bearing unnatural amino acid would allow for the efficient preparation of a variety of drug conjugates via azide-alkyne cycloaddition. In support of this strategy, a dimeric version of EETI 2.5F which tolerated the substitution of an unnatural amino acid containing an amino-oxy group at position 15 was recently described. We therefore prepared the azido-variant EETI 2.5Z via solid-phase peptide synthesis and showed that it retained low-nanomolar binding affinity to U87MG (glioblastoma) cells.

Example 2—Preparation of Knottin-Drug Conjugates

A cytotoxic payload was sought that could be efficiently conjugated to EETI-2.5Z in order to demonstrate proof-of-concept of knottins as vehicles for targeted drug delivery. The nucleoside analogue Gemcitabine was identified as a possible candidate given its precedence as a chemotherapeutic, its potency against a variety of malignant cell lines, and its tractable derivatization from inexpensive starting materials.

Alkyne-bearing Gemcitabine derivatives tethered via several functional groups including an ester (derivative 4a), a carbamate (derivative 4b), and an amide (derivative 4c) were prepared. Additionally, given the use of dipeptide-based cleavable linkers in ADCs, a Val-Ala-PAB (valyl-alanyl-para-aminobenzyloxy) derivative was prepared (derivative 4d) which employs a linker that is stable in the extra-cellular environment but which is cleaved rapidly upon internalization by proteases such as cathepsin B. Each of these Gemcitabine derivatives were then linked to EETI 2.5Z via copper-catalyzed azide-alkyne cycloaddition (FIG. 3, Panel B) to produce the corresponding EETI 2.5Z-Gemcitabine conjugates (5a-d), where: "5a" designates the conjugate having the ester linker; "5b" designates the conjugate having the carbamate linker; "5c" designates the conjugate having the amide linker; and "5d" designates the conjugate having the Val-Ala-PAB linker.

Example 3—Binding Affinities and Potencies of Knottin-Drug Conjugates

Figure 4:
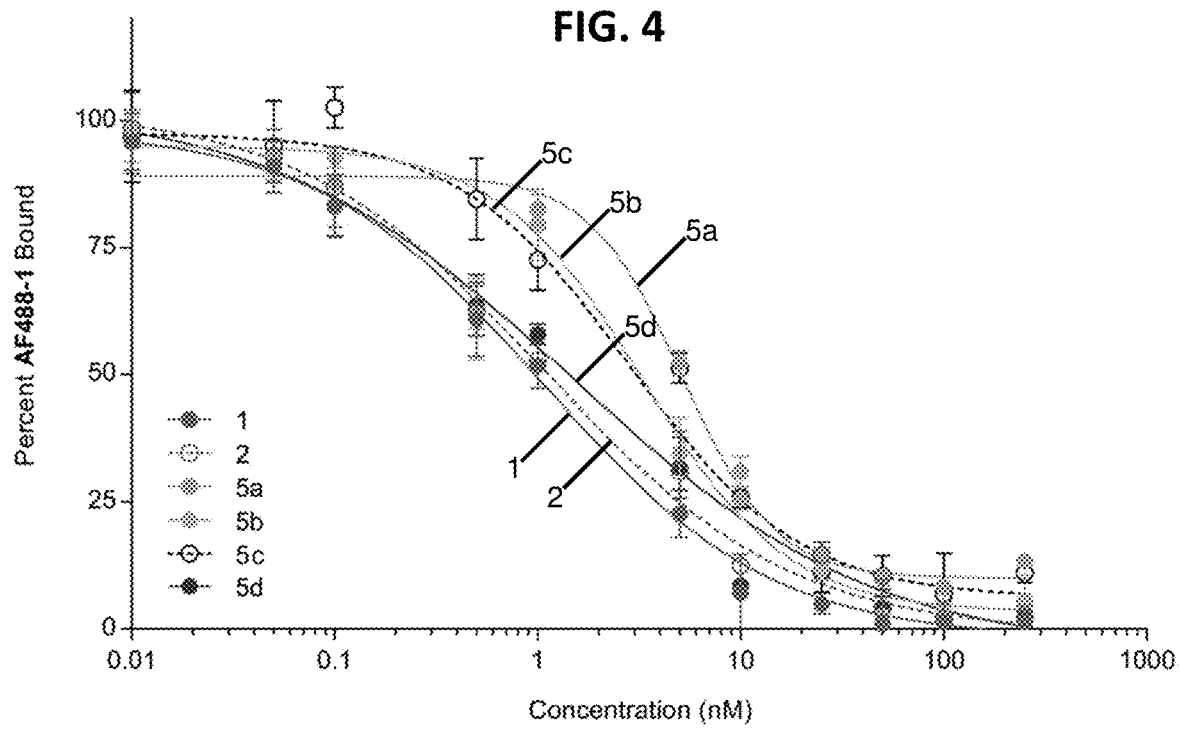
FIG. 4 shows binding of 1, 2, and 5a-d to U87MG cells.

Once the knottin-drug conjugates 5a-d were prepared, their binding affinity to U87MG glioblastoma cells, which are known to have elevated expression of tumor-associated integrins, was tested. FIG. 4 shows binding of 1, 2, and 5a-d to U87MG cells. To measure the relative binding affinities of knottins 1 and 2 and KDCs 5a-d, competition binding assays were performed using AlexaFluor 488-conjugated EETI-2.5F (AF488-1) as previously described (J. W. Kim, et al., *J. Am. Chem. Soc.* 2015, 137, 6-9). Cells ($5\times10^4$ per sample) were detached with 0.05% Trypsin-EDTA, washed with IBB (25 mM Tris pH 7.4, 150 mM NaCl, 2 mM $CaCl_2$, 1 mM $MgCl_2$, 1 mM $MnCl_2$, and 0.1% bovine serum albumin), and incubated with 1 nM AF488-1 and varying concentrations of competitors in 800 µL of IBB at 4° C. for 3 hours. The cells were washed twice with 800 µL of PBSA (phosphate buffered saline containing 0.1% bovine serum albumin) and the fluorescence of the surface-bound AF488-1 was determined using flow cytometry. The fluorescence was normalized to that of cells treated with AF488-1 alone to obtain the fraction bound. Half-maximal inhibitory concentration ($IC_{50}$) values were determined by nonlinear regression analysis. Error bars represent the standard deviation of experiments performed in triplicate.

As shown in Table 3, all KDCs tested bound to U87MG cells with low-nanomolar affinity, indicating that the presence of the linker and drug do not interfere with the ability of the knottin to target tumor cells.

Figure 5:
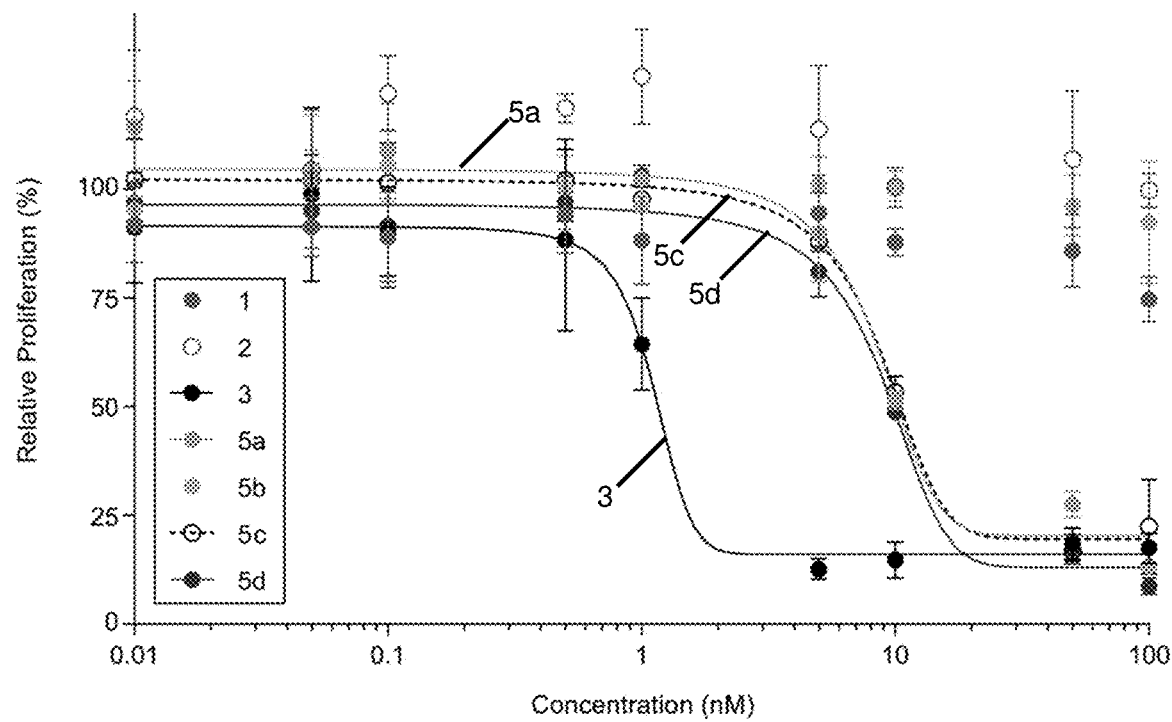
FIG. 5 illustrates potency of 1, 2, 3, and 5a-d in U87MG Cells.

Next, the potency of each KDC was tested in a cell-proliferation experiment. FIG. 5 shows the potency of 1, 2, 3, and 5a-d in U87MG cells. Cells were seeded in a 96-well plate at a density of 2,500 cells per well and grown overnight at 37° C., 5% $CO_2$ in DMEM with 10% FBS and 1% penicillin/streptomycin. Cells were subsequently treated with 100 µL of fresh media, containing varying concentrations of drug, protein, or protein-drug conjugate and incubated for 4 d at 37° C., 5% $CO_2$. Cell proliferation was measured according to the method described in Section 1.3. Error bars represent the standard deviation of experiments performed in triplicate. It was found that KDCs with linkers containing the ester (5a), amide (5c), and Val-Ala-PAB (5d) moieties demonstrated low-nanomolar $ED_{50}$ values in U87MG cells, similar to unconjugated Gemcitabine (3). In contrast, unlabeled EETI-2.5Z (2) did not show significant growth-inhibition activity, indicating that the conjugation of Gemcitabine is necessary for potency. Moreover, the KDC containing the carbamate linker (5b) also lacked significant potency. Given that the linker must be cleaved to release free Gemcitabine in order for the payload to become active, the low potency of 5b can be explained by the greater stability of the carbamate group as compared to the other linkers tested.

TABLE 3

Binding Affinity & Potency of KDCs in U87MG Cells

| # | Compound | $IC_{50}$ (nM)[a] | $ED_{50}$ (nM)[b] |
|---|---|---|---|
| 1 | 2 | EETI-2.5Z w/o drug | 1.1 ± 1.8 | >1,000 |
| 2 | 5a | ester linker | 5.2 ± 3.6 | 8.5 ± 3.3 |
| 3 | 5b | carbamate linker | 3.3 ± 0.2 | >1,000 |
| 4 | 5c | amide linker | 2.8 ± 0.2 | 8.9 ± 1.2 |
| 5 | 5d | Val-Ala-PAB linker | 1.5 ± 0.2 | 9.0 ± 1.8 |
| 6 | 3 | Gemcitabine | N/A | 1.1 ± 1.4 |

[a]Cells bound w/ AF488-labeled 1 were titrated with each compound and percent bound was measured by flow cytometry.
[b]Cell proliferation was quantified using CCK-8 colorimetric assays and compared to untreated control.

Example 4—Drug Release Characterization

Figure 6:
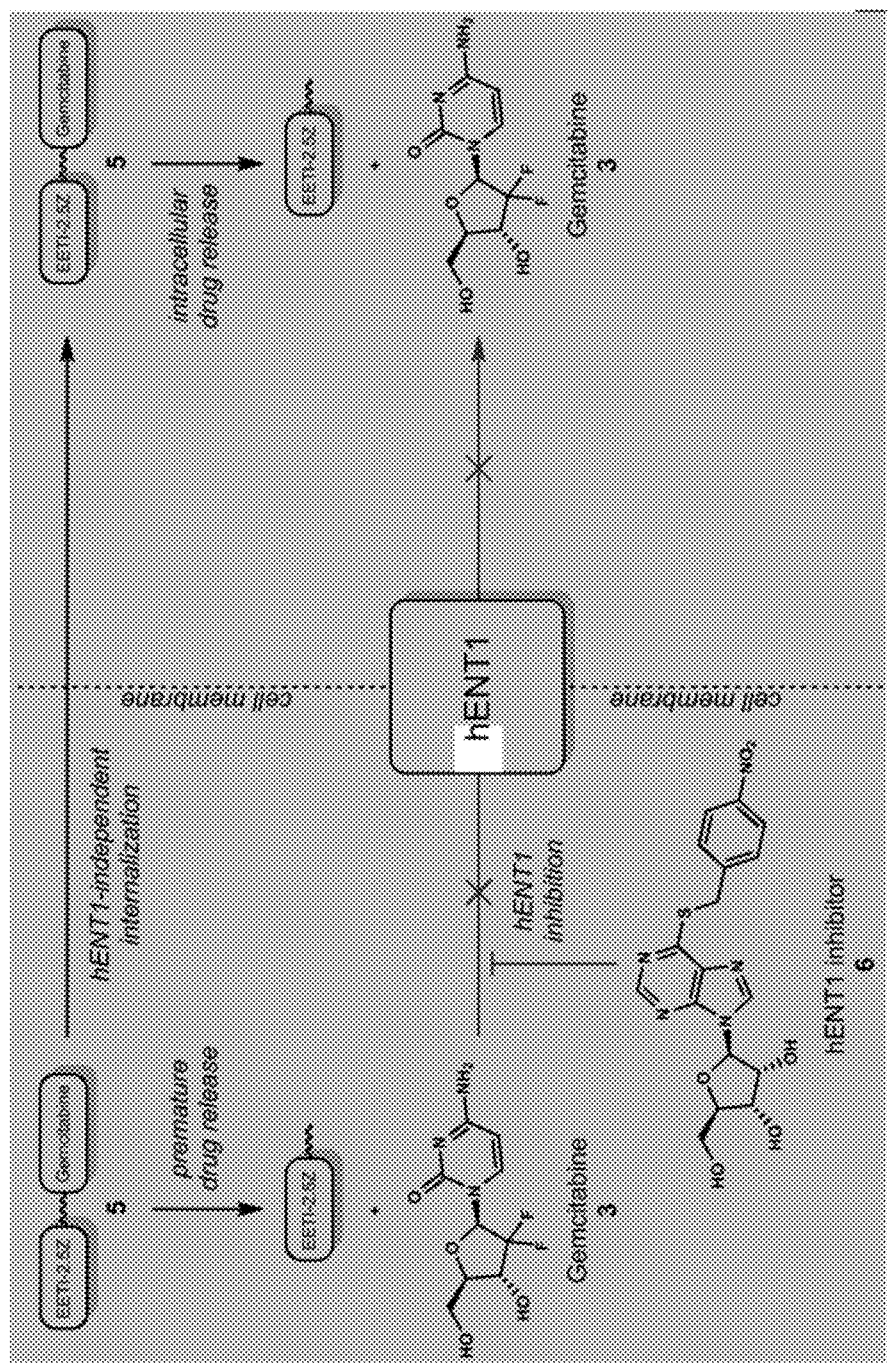
FIG. 6 depicts a scheme for study of premature drug release via hENT1 inhibition.

The relative extent of premature drug-release in the cases of 5a, 5c, and 5d was next determined in order to identify the linker best-suited for delivering the drug payload intracellularly. An established technique for blocking the cellular uptake of Gemcitabine by using S (4-nitrobenzyl)-6-thioinosine (6) was employed, which is known to inhibit human equilibrative nucleoside transporters, such as hENT1. Because hENT1 is a critical regulator of the cellular internalization of Gemcitabine, it was reasoned that by inhibiting its activity with 6, the cytotoxic effect of any drug payload that was released in the extracellular environment could be diminished. It was anticipated that this would allow the distinction between KDCs that were potent due to the undesirable release of Gemcitabine outside of the cell from those that released Gemcitabine intracellularly (FIG. 6). The extent of premature drug release in the extracellular environment was studied by inhibiting activity of nucleoside transporters (such as hENT1) of U87MG cells through the use of the hENT1 inhibitor S-(4-nitrobenzyl)-6-thioinosine (6). By inhibiting the activity of hENT1 with increasing concentrations of 6, the $ED_{50}$ of unconjugated gemcitabine (3) was shown to increase (vide infra). In a similar fashion, it was expected that for KDCs which released a significant amount of the drug payload in the extracellular environment, an increase in the concentration of 6 should result in a concomitant increase in $ED_{50}$ value. Un-optimized drug conjugates were therefore expected to generate $ED_{50}$ values that increased significantly with increasing concentrations of 6; desirable drug conjugates were expected to maintain low $ED_{50}$ values even when high doses of 6 were co-administered.

Figure 7:
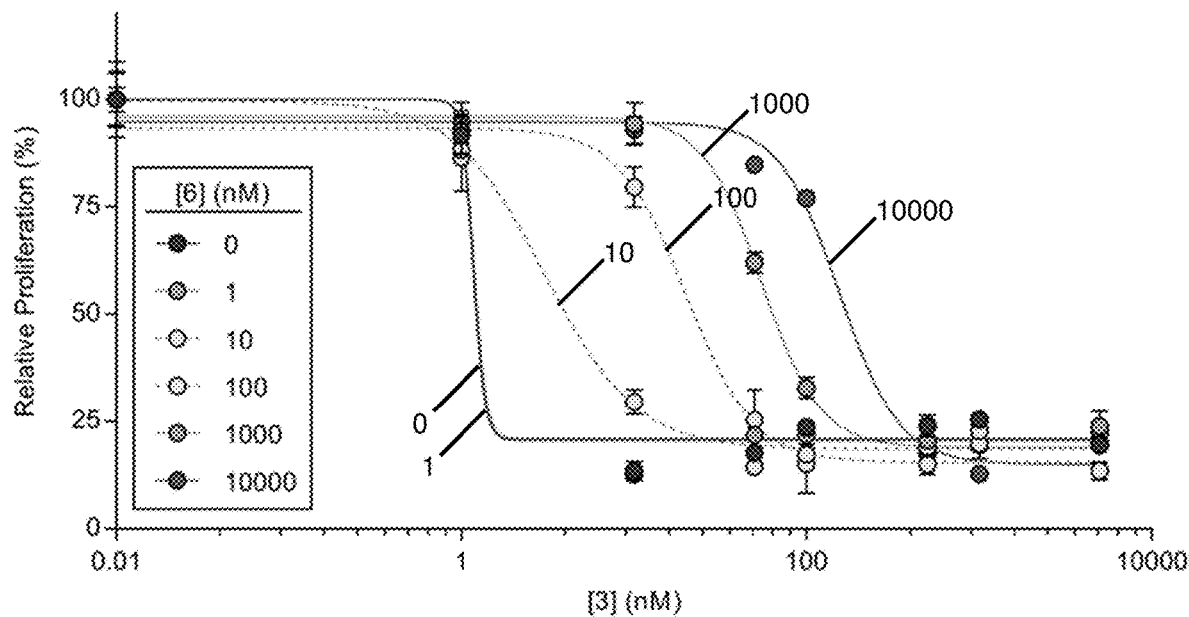
FIG. 7 illustrates the effect of 6 on $ED_{50}$ of 3 in U87MG cells.
Figure 8:
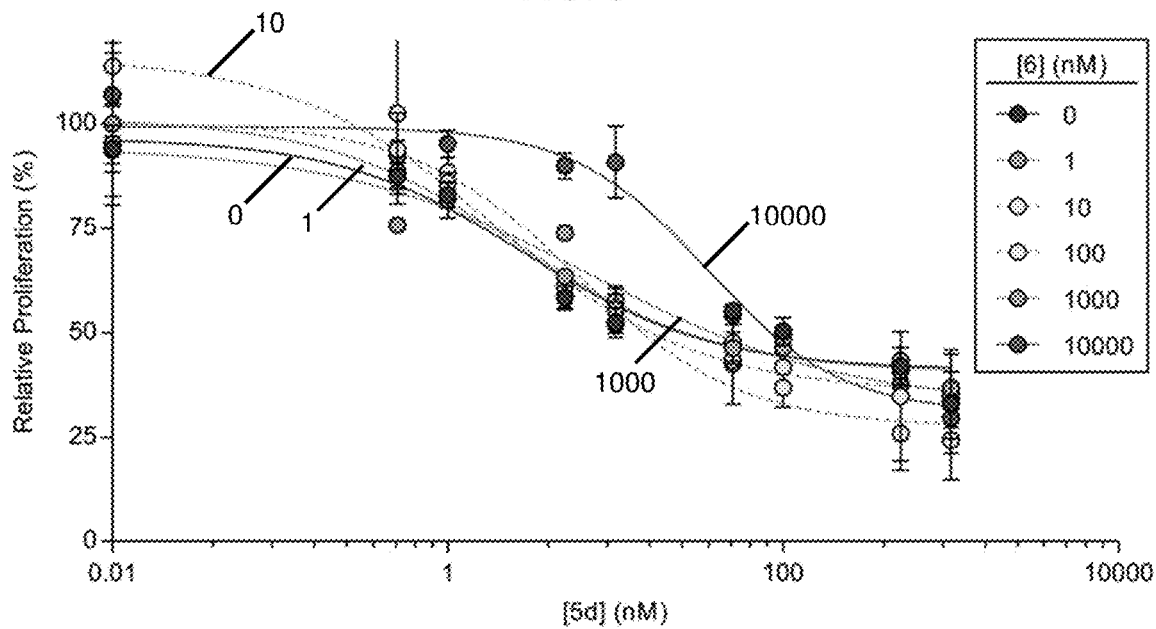
FIG. 8 illustrates the effect of 6 on $ED_{50}$ of 5d in U87MG cells.

Media used to prepare varying concentrations of drug, protein, or protein-drug conjugate also contained varying concentrations of the hENT1 inhibitor, 6. Additionally, prior to treatment, cell were incubated at 37° C., 5% $CO_2$ with fresh media containing the varying concentrations of 6 for 2 h. Cell proliferation was measured using the Cell Counting Kit-8 by replacing the media in each well with 100 µL of media containing 10% WST-8. After incubation for 1 h at 37° C., absorbance at 450 nm was measured with a Synergy H4 microtiter plate reader. $ED_{50}$ values were determined by nonlinear regression analysis. Example dose-response curves for 3 (FIG. 7) and 5d (FIG. 8) are provided. Cell proliferation was measured according to the method described in Section 1.3. Error bars represent the standard deviation of experiments performed in triplicate.

TABLE 4

Effect of [6] on ED50 for 3, 5a, 5c, and 5d in U87MG Cells.

| | | $ED_{50}$ in U87MG Cells | | |
|---|---|---|---|---|
| [6] (nM) | 3 gemcitabine | 5a ester linker | 5c amide linker | 5d Val-Ala-PAB linker |
| 0 | 1.2 ± 0.1 | 9.7 ± 0.1 | 12.6 ± 1.0 | 3.9 ± 4.0 |
| 1 | 1.4 ± 0.5 | 20.2 ± 4.7 | 18.8 ± 2.3 | 2.7 ± 1.2 |
| 10 | 3.0 ± 0.1 | 40.3 ± 2.9 | 24.9 ± 2.5 | 1.5 ± 2.5 |
| 100 | 20.1 ± 0.4 | 150.5 ± 5.2 | 110.8 ± 60.3 | 6.2 ± 4.0 |
| 1000 | 54.8 ± 0.4 | 183.4 ± 0.2 | 239.0 ± 65.9 | 8.7 ± 4.5 |
| 10000 | 155.5 ± 3.4 | 1316.6 ± 3.9 | 404.6 ± 63.9 | 35.4 ± 20.9 |

$ED_{50}$ values of 3, 5a, 5c, and 5d for each concentration of 6 are provided in Table 4. These values were normalized as Fold Increase in $ED_{50}$ (defined in Equation 2) by dividing the $ED_{50}$ of each drug when 6 was co-administered at concentration=C by the $ED_{50}$ of that same drug when no 6 was added, then subtracting 1 (thus, a "0-fold increase" would mean no increase, while a "1-fold increase" would mean that the $ED_{50}$ value had doubled). Fold Increase in $ED_{50}$ for each drug at each concentration of 6 is provided in Table 5, and these values were used to generate FIG. 9.

Fold Increase in $ED_{50}$ $$\text{Fold Increase in } ED_{50} = \frac{ED_{50([6]=C)}}{ED_{50([6]=0)}} - 1. \quad \text{Equation 2}$$

TABLE 5

Effect of [6] on Fold Increase in ED50 for 3, 5a, 5c, and 5d in U87MG Cells.

| | Fold Increase in $ED_{50}$ in U87MG Cells | | | |
|---|---|---|---|---|
| [6] (nM) | 3 gemcitabine | 5a ester linker | 5c amide linker | 5d Val-Ala-PAB linker |
| 0 | 0 | 0 | 0 | 0 |
| 1 | 0.2 ± 0.4 | 1.1 ± 0.5 | 0.5 ± 0.2 | −0.3 ± 0.3 |
| 10 | 1.5 ± 0.1 | 3.2 ± 0.3 | 1.0 ± 0.2 | −0.6 ± 0.6 |
| 100 | 15.8 ± 0.3 | 14.5 ± 0.5 | 7.8 ± 4.8 | 0.6 ± 1.0 |
| 1000 | 44.7 ± 0.3 | 17.9 ± 0.0 | 18.0 ± 5.2 | 1.2 ± 1.2 |
| 10000 | 128.6 ± 2.8 | 134.7 ± 0.4 | 31.1 ± 5.1 | 8.1 ± 5.4 |

Figure 9:
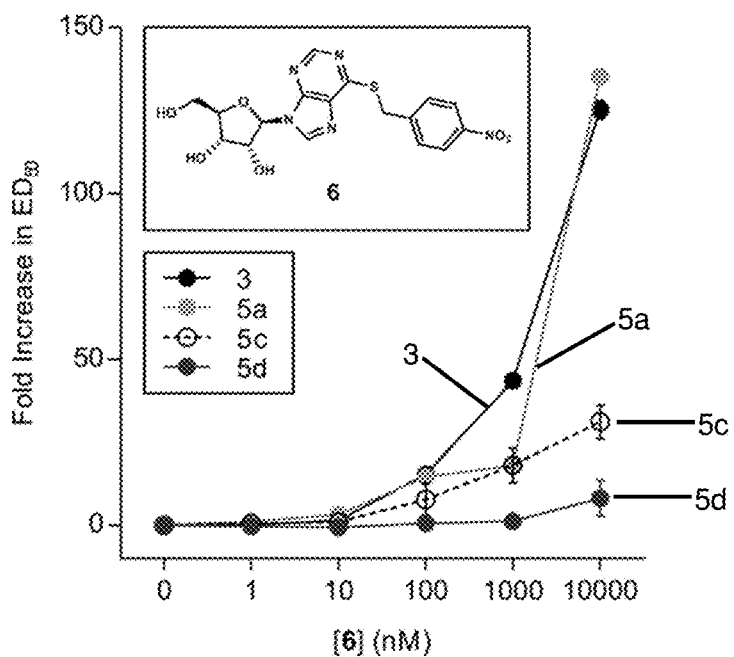
FIG. 9 shows data indicating that inhibition of hENT1 by S-(4-nitrobenzyl)-6-thioinosine diminishes potency of Gemcitabine, as well as a knottin-drug conjugate (KDC) having an ester linker, and a KDC having an amide linker, but has little effect on potency of a KDC having a Val-Ala-PAB linker.

As shown in FIG. 9, the $ED_{50}$ values of unconjugated Gemcitabine as well as KDC 5a in U87MG cells increased significantly when cells were treated with increasing concentrations of 6.

These results indicate that in the case of 5a, a significant amount of the linker is cleaved prematurely outside of the cell, and that the released Gemcitabine is still reliant upon hENT1 activity for cellular uptake. However, in the case of 5c and 5d, it was found that potency was much less sensitive to the concentration of 6. In particular, treatment with 6 appeared to have no effect on the potency of EETI-2.5Z-Val-Ala-PAB-gemcitabine (5d) except when the highest dose of 6 (10 µM) was used. This suggests that the mechanism of internalization of the drug payload in the case of 5d is independent of hENT1, indicative of minimal premature drug release.

Example 5—Effect of Integrin Blocking on Potency

Figure 10:
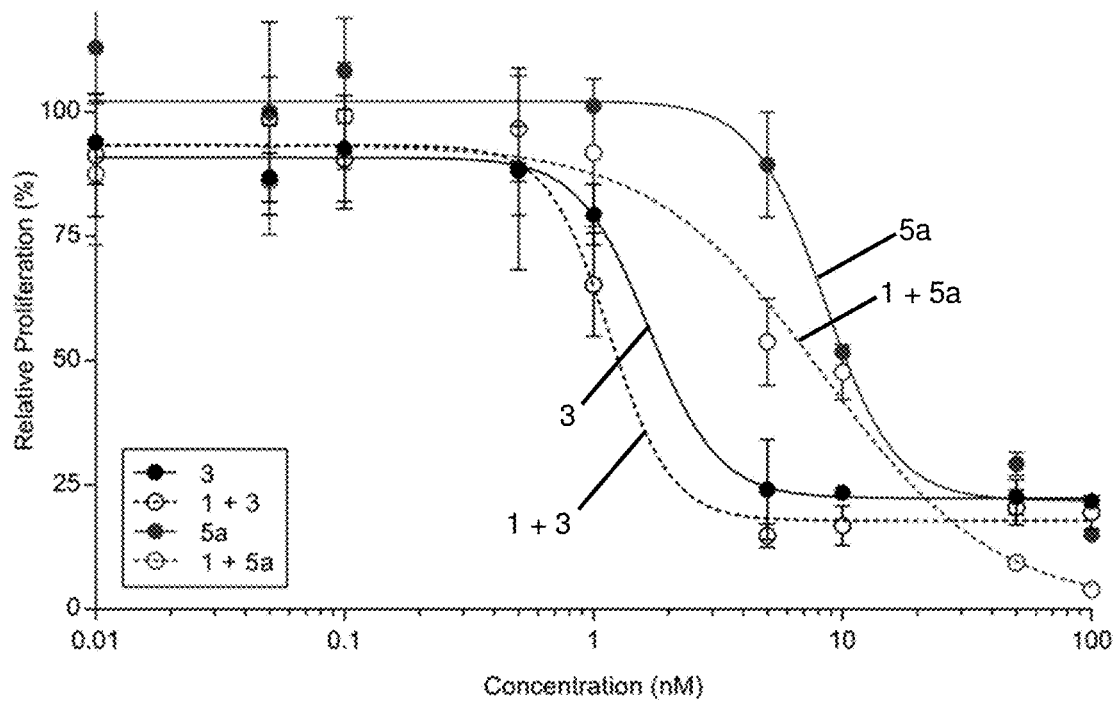
Figure 11:
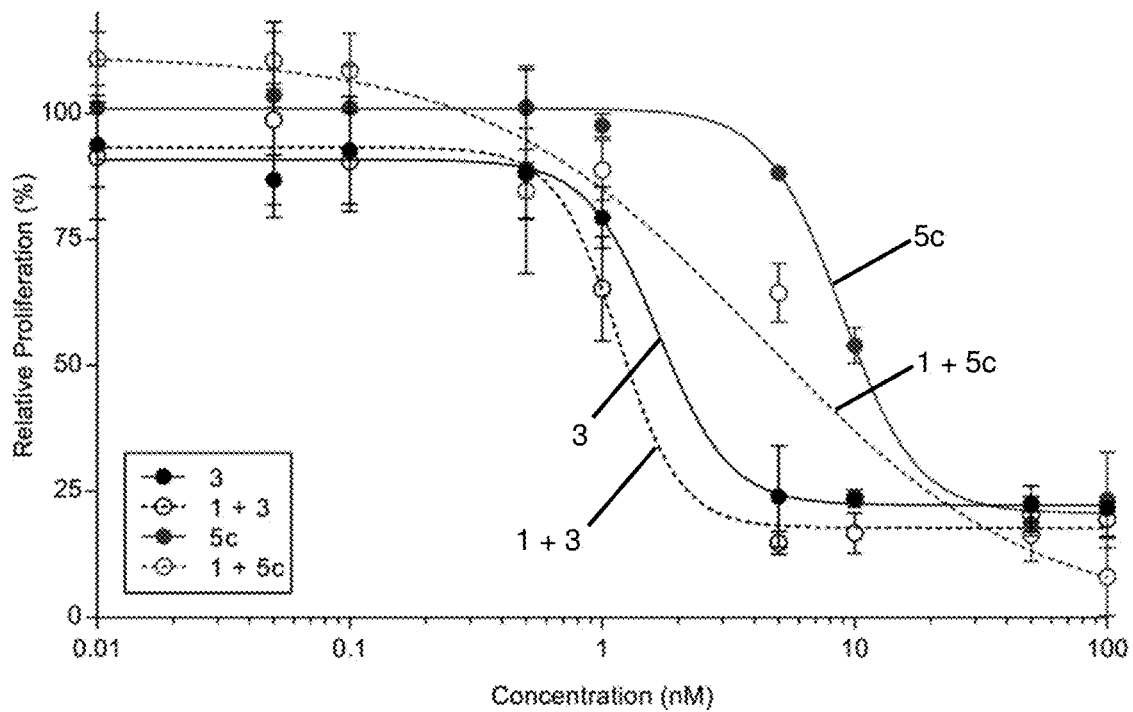
FIG. 11 shows that integrin-blocking with 1 does not decrease potency of 5c.
Figure 12:
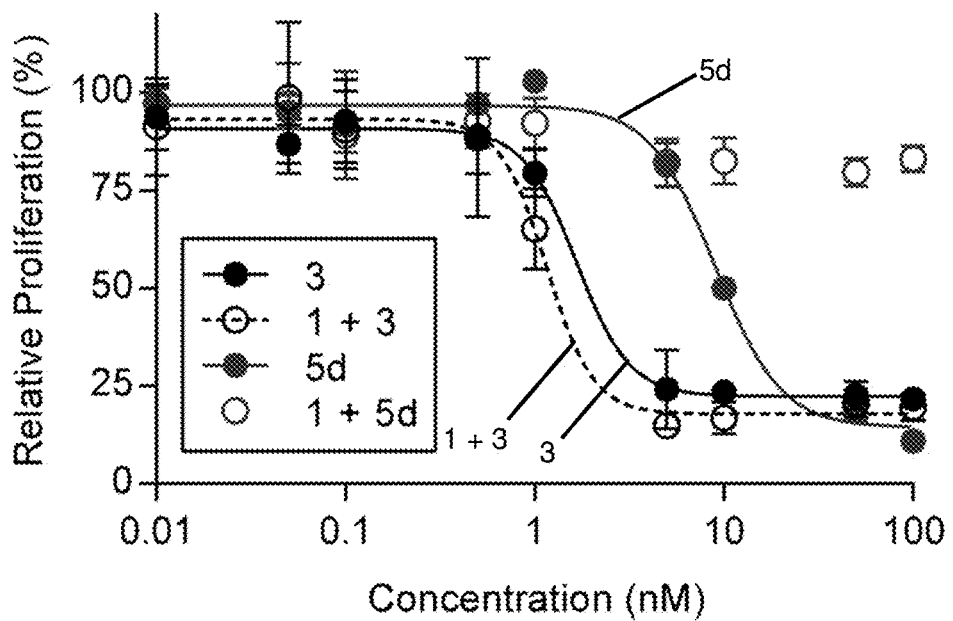
FIG. 12 shows data indicating that integrin-blocking of U87MG cells by EETI-2.5F significantly reduces potency of a KDC having a Val-Ala-PAB linker but has no effect on potency of Gemcitabine.
Figure 13:
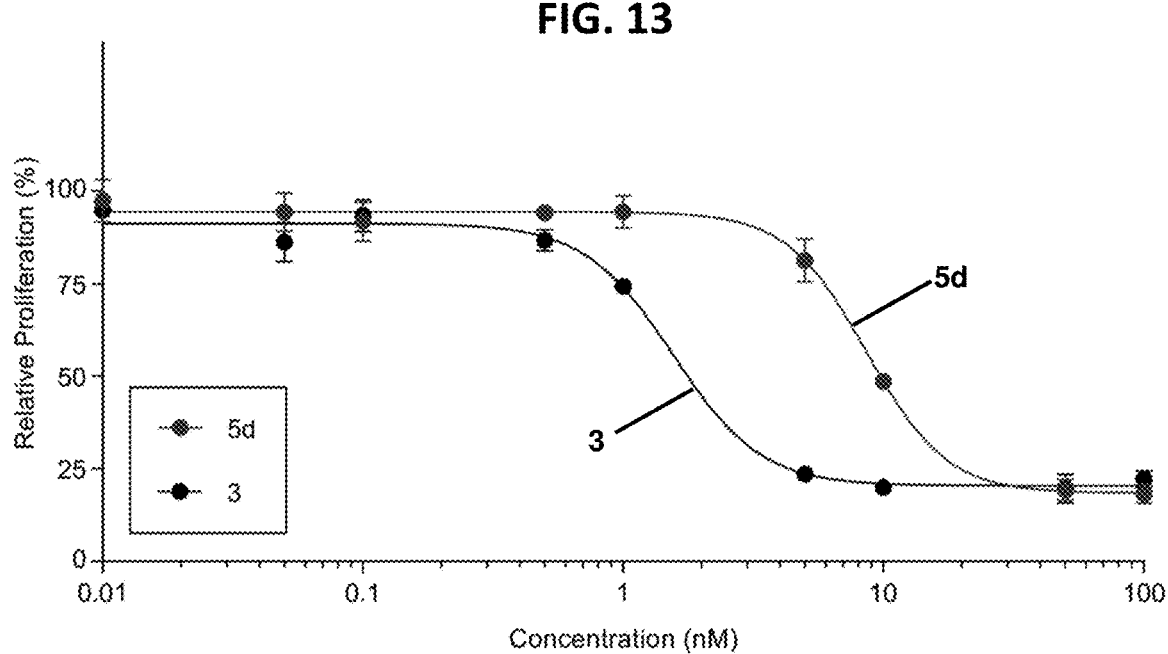
FIG. 13 shows potency of 3 and 5d in D270 glioblastoma cells.
Figure 14:
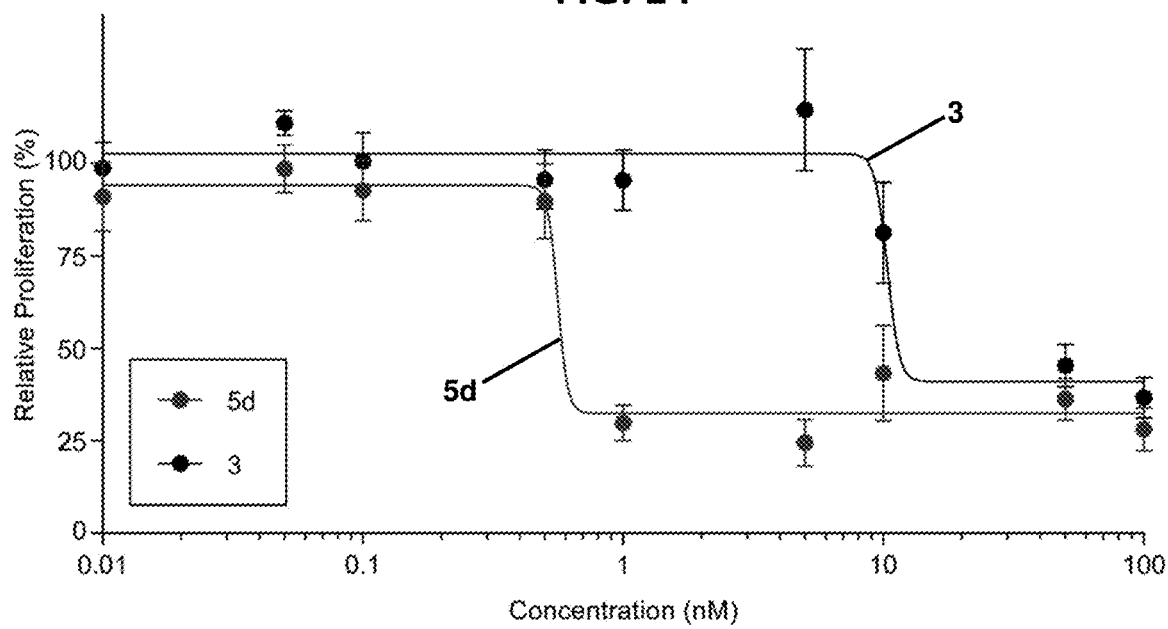
FIG. 14 shows potency of 3 and 5d in MDA-MB-468 breast cancer cells.
Figure 15:
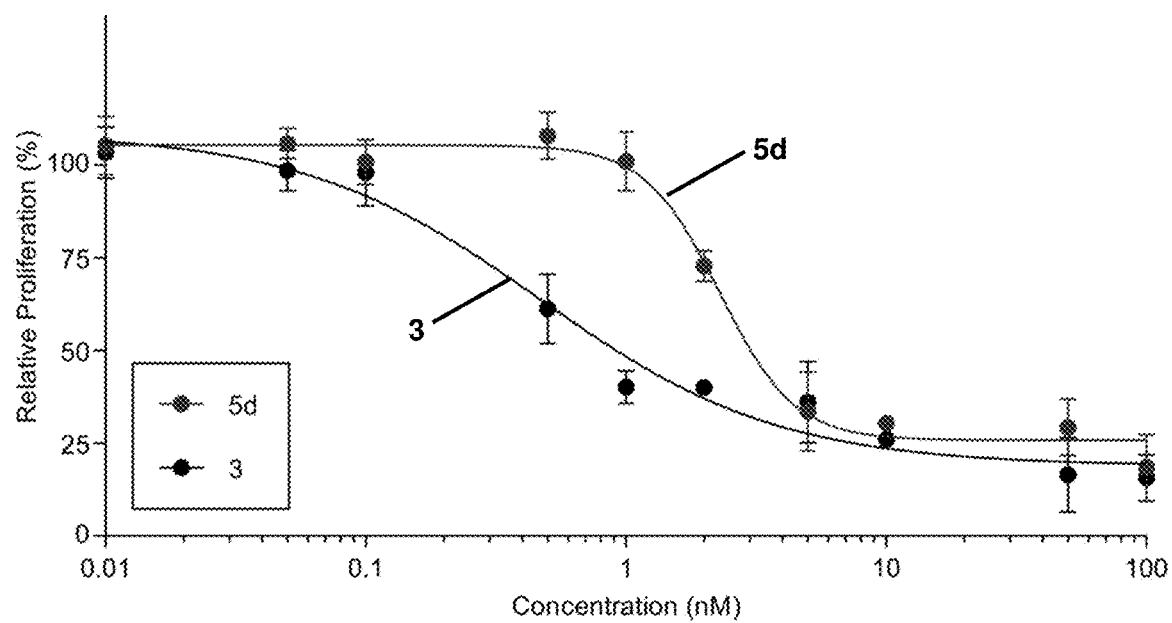
FIG. 15 shows potency of 3 and 5d in A2780 ovarian cancer cells.
Figure 16:
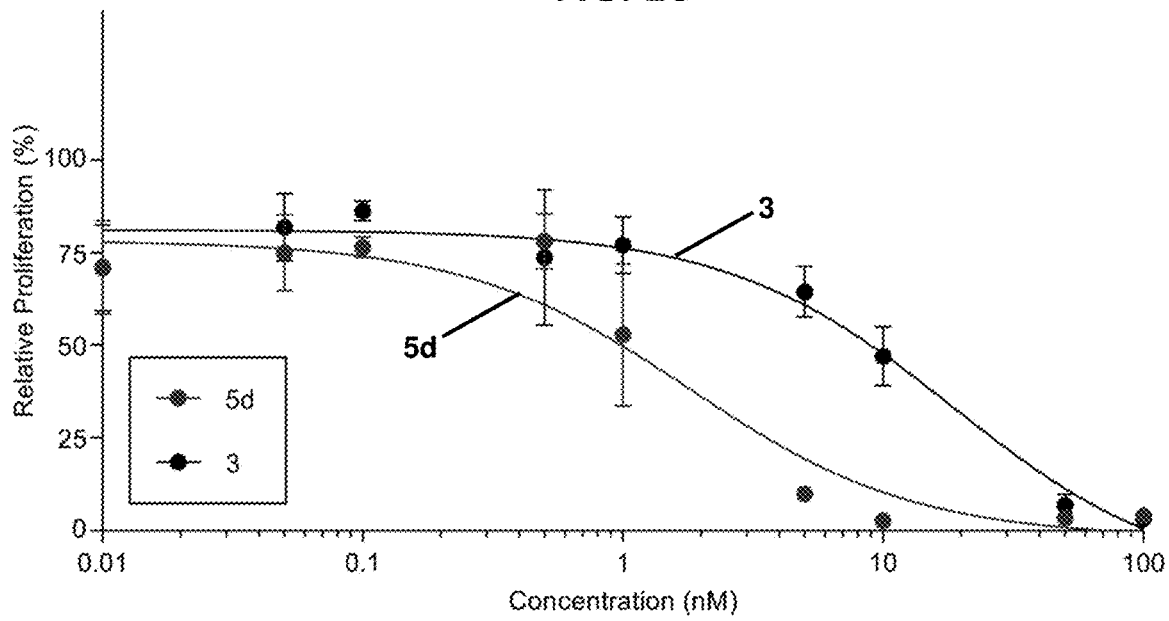
FIG. 16 shows potency of 3 and 5d in BxPC3 pancreatic cancer cells.
Figure 17:
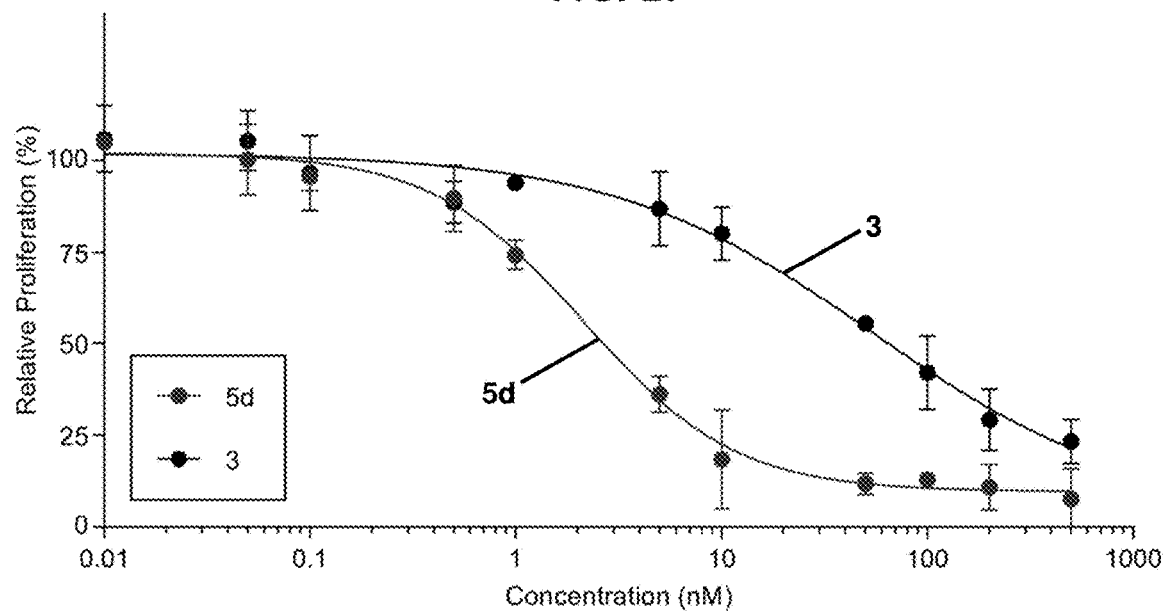
FIG. 17 shows potency of 3 and 5d in PANC-1 pancreatic cancer cells.

One possible explanation for the apparent hENT1-independence of 5d is that its route of internalization could be integrin-mediated. The role of integrin-binding in the biological potency and hENT1-independence of 5d was determined. A competition experiment was carried out in which U87MG cells were pre-treated with unconjugated EETI-2.5F (1) in order to block integrins on the cell surface. The role of integrin-binding was studied by measuring the proliferation of U87MG cells that had been pre-treated with EETI-2.5F (1) when exposed to increasing doses of 3 and KDCs 5a, 5c, and 5d. By saturating the tumor-associated integrins targeted by the KDCs using a competitor knottin bearing no drug payload, KDCs such as 5a (FIG. 10) and 5c (FIG. 11) which did not rely upon integrin-binding for potency could be distinguished from those where integrin-binding was critical for potency, such as 5d (FIG. 12). Media used to prepare varying concentrations of drug, protein, or protein-drug conjugate also contained 1 µM of 1. Prior to treatment, cells were incubated for 3 h at 37° C., 5% $CO_2$ with fresh media containing 1 µM 1. After this pre-treatment, cells were incubated with varying concentrations of 5a, 5c, or 5d for 24 h and then media was replaced with fresh media and cells were incubated for an additional 48 h. Cell proliferation was measured using the Cell Counting Kit-8 by replacing the media in each well with 100 µL of media containing 10% WST-8. After incubation for 1 h at 37° C., absorbance at 450 nm was measured with a Synergy H4 microtiter plate reader. Cell proliferation was measured according to the method described in Section 1.3. Error bars represent the standard deviation of experiments performed in triplicate.

In agreement with the hENT1-inhibition experiment, it was found that pre-treatment with 1 did not diminish the potency of 5a and 5c. This suggests that for these KDCs, integrin-binding is not essential for internalization of the payload, consistent with a case where potency results primarily from premature drug release. In stark contrast, it was found that pre-treatment of U87MG cells with 1 abolishes the potency of KDC 5d, even at the highest concentration tested (FIG. 12). This suggests that for 5d, integrin-binding is a critical part of the mechanism by which it delivers its cytotoxic payload, consistent with integrin-mediated internalization followed by intracellular drug-release.

Taken together, the results shown in Table 3 and FIGS. 9 and 12 suggest that KDC 5d: 1) targets cells based on the expression of tumor-associated integrins, 2) is internalized via a mechanism that relies upon integrin binding, and 3) releases its drug payload in significant amounts only upon intracellular degradation of the linker, likely by lysosomal proteases such as cathepsin B.

Example 6—Effect of Integrin Blocking on the Potency of a Cleavable Linker-Containing Knottin-Drug Conjugate Having identified KDC 5d as a potent inhibitor of U87MG cells with desirable payload-release properties, its efficacy against a variety of other cell lines in comparison with Gemcitabine (3) was next tested. Cells were seeded in a 96-well plate at a density of 2,500 cells per well and grown overnight at 37° C., 5% $CO_2$ in the media described in Section 1.3. Cells were subsequently treated with 100 μL of fresh media, containing 50 nM of 3 or 5d. Cells were incubated at 37° C., 5% $CO_2$ for 4 d. Cell proliferation was measured using the Cell Counting Kit-8 by replacing the media in each well with 100 μL of media containing 10% WST-8. After incubation for 1 h at 37° C., absorbance at 450 nm was measured with a Synergy H4 microtiter plate reader. Cell proliferation was measured according to the method described in Section 1.3. Error bars represent the standard deviation of experiments performed in triplicate. See FIGS. 13-18.

Figure 18:
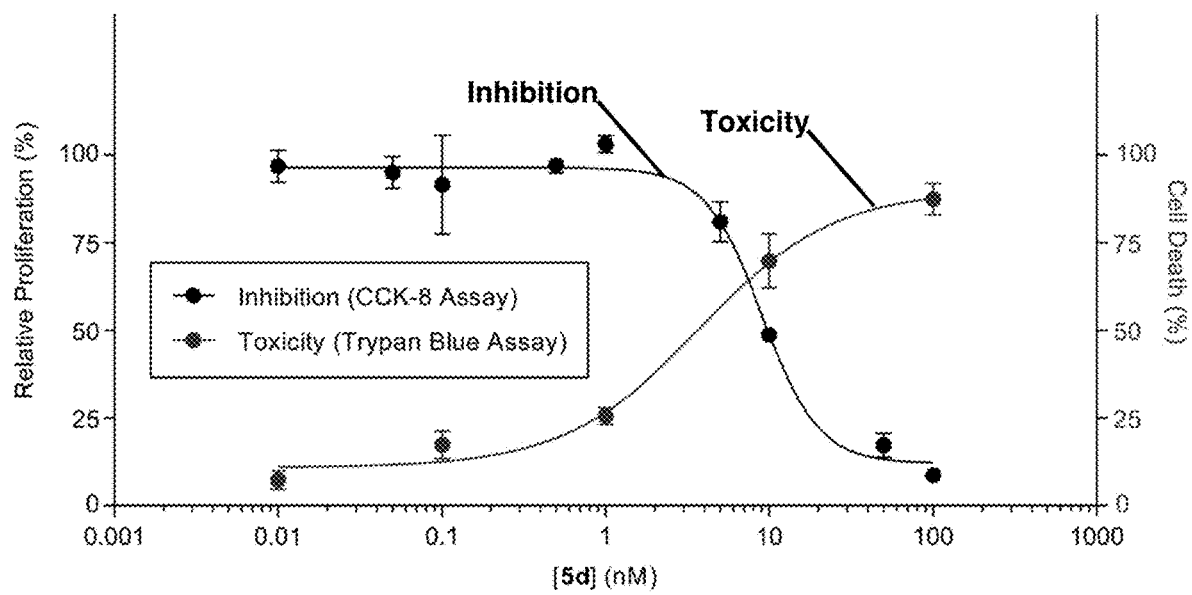
FIG. 18 shows percent cell death vs. relative proliferation of U87-MG cells.

To validate use of the CCK-8 metabolic assay to determine potency of KDCs in tumor cells, a comparison was made using a Trypan Blue exclusion test. U87-MG cells were seeded in a 96-well plate at a density of 2,000 cells per well and grown overnight at 37° C., 5% $CO_2$ in DMEM with 10% FBS and 1% penicillin/streptomycin. Cells were subsequently treated with 100 μL of fresh media, containing varying concentrations of 5d and incubated for 3 d at 37° C., 5% $CO_2$. Cell toxicity was assessed using exclusion of Trypan Blue. Media was removed from each well and cells adhering to the bottom of each well were washed using 100 μL of PBS. After removal of the PBS wash, cells were detached using 0.05% Trypsin-EDTA and pelleted. Cells were then stained by re-suspension in 0.2% Trypan Blue (diluted using PBS). Living cells excluded Trypan blue while dead cells were stained. Living and dead cells were then counted using a hemocytometer and the percent cell death was calculated according to Equation 3. FIG. 18 depicts Percent Cell Death plotted alongside Relative Proliferation (black; measured using the CCK-8 assay described in Section 1.3. Error bars represent the standard deviation of 3 wells counted.

Percent Cell Death $$\text{Cell Death} = \frac{\text{Dead Cells}}{\text{Dead Cells} + \text{Live Cells}} \times 100\% \qquad \text{Equation 3}$$

As shown in Table 6 (entries 2-5), 5d is also a highly potent inhibitor of D270 glioblastoma, MDA-MB-468 breast cancer, A2780 ovarian cancer, and BxPC3 pancreatic cancer cell lines.

TABLE 6

Cell growth inhibition by KDC (5d) vs. Gemcitabine (3).[a]

|   | Cell Line | Cancer Type | 5d $ED_{50}$ (nM) | 3 $ED_{50}$ (nM) |
|---|---|---|---|---|
| 1 | U87MG | glioblastoma | 9.0 ± 1.8 | 1.7 ± 1.4 |
| 2 | D270 | glioblastoma | 7.9 ± 0.8 | 1.5 ± 0.4 |
| 3 | MB-468 | breast | 0.6 ± 0.1 | 17.3 ± 6.8 |
| 4 | A2780 | ovarian | 2.3 ± 0.5 | 0.5 ± 0.02 |
| 5 | BxPC3 | pancreatic | 1.8 ± 0.8 | 18.4 ± 1.3 |
| 6 | PANC-1 | pancreatic | 2.1 ± 0.2 | 52.8 ± 4.9 |

[a]Cell proliferation was quantified 4 d after treatment with 5d or 3 using CCK 8 colorimetric assays and compared to untreated control.

The high potency of 5d against PANC-1 pancreatic cancer cells (Table 6 entry 6) is particularly noteworthy given the high resistance of this cell line to Gemcitabine, which is thought to be associated with its diminished nucleoside transporter activity. It is possible that the significantly higher potency of 5d against this cell line results from an alternative, integrin-mediated pathway for cellular uptake, obviating reliance on transporters such as hENT1.

Accordingly, the preceding merely illustrates the principles of the present disclosure. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A knottin-drug conjugate, comprising:
   a knottin peptide comprising an engineered loop that binds to a receptor on a cancer cell surface; and
   a chemotherapeutic nucleoside drug conjugated to the knottin peptide through an intracellularly cleavable linker.

2. The knottin-drug conjugate of claim 1, wherein the knottin peptide is selected from the group consisting of: an EETI-II peptide, an AgRP peptide, a ω-conotoxin peptide, a Kalata B1 peptide, an MCoTI-II peptide, an agatoxin peptide, and a chlorotoxin peptide.

3. The knottin-drug conjugate of claim 1, wherein the receptor is a cell adhesion receptor.

4. The knottin-drug conjugate of claim 3, wherein the cell adhesion receptor is an integrin.

5. The knottin-drug conjugate of claim 4, wherein the integrin is selected from the group consisting of: αvβ1 integrin, αvβ3 integrin, αvβ5 integrin, αvβ6 integrin, α5β1 integrin, and any combination thereof.

6. The knottin-drug conjugate of claim 1, wherein the receptor is a chemokine receptor.

7. The knottin-drug conjugate of claim 6, wherein the chemokine receptor is C-X-C chemokine receptor type 4 (CXCR4).

8. The knottin-drug conjugate of claim 1, wherein the receptor is a growth factor receptor.

9. The knottin-drug conjugate of claim 1, wherein the receptor is an immune cell receptor.

10. The knottin-drug conjugate of claim 9, wherein the immune cell receptor is cytotoxic T-lymphocyte-associated protein 4 (CTLA-4).

11. The knottin-drug conjugate of claim 1, wherein the receptor is neuropilin-1 (NRP1).

12. The knottin-drug conjugate of claim 1, wherein the chemotherapeutic nucleoside drug comprises a nucleoside analogue.

13. The knottin-drug conjugate of claim 12, wherein the nucleoside analogue is selected from the group consisting of: gemcitabine, cytarabine, troxacitabine, decitabine, cladribine, fludarabine, clofarabine, and 2'-C-cyano-2'-deoxy-1-β-D-arabino-pentofuranosylcytosine (CNDAC).

14. The knottin-drug conjugate of claim 13, wherein the nucleoside analogue is gemcitabine.

15. The knottin-drug conjugate of claim 1, wherein the intracellularly cleavable linker is a dipeptide-based intracellularly cleavable linker.

16. The knottin-drug conjugate of claim 15, wherein the dipeptide-based intracellularly cleavable linker is a valyl-alanyl-para-aminobenzyloxy (Val-Ala-PAB)-based intracellularly cleavable linker.

17. The knottin-drug conjugate of claim 1, wherein the knottin peptide comprises an unnatural amino acid to which the linker is attached.

18. The knottin-drug conjugate of claim 17, wherein, prior to attachment, the unnatural amino acid comprises a functional group selected from the group consisting of: an azide, alkyne, alkene, amino-oxy, hydrazine, aldehyde, asaldehyde, nitrone, nitrile oxide, cyclopropene, norbornene, isocyanide, aryl halide, boronic acid, diazo, tetrazine, tetrazole, quadrocyclane, and iodobenzene.

19. The knottin-drug conjugate of claim 18, wherein, prior to attachment, the unnatural amino acid comprises an azide functional group.

20. A pharmaceutical composition comprising:
   the knottin-drug conjugate of claim 1; and
   a pharmaceutically-acceptable excipient.

21. The pharmaceutical composition of claim 20, wherein the composition is formulated for parenteral administration.

22. The pharmaceutical composition of claim 20, wherein the composition is formulated for oral administration.

23. A kit comprising:
a therapeutically effective amount of the pharmaceutical composition of claim 20; and
instructions for administering the pharmaceutical composition to an individual in need thereof.

24. The kit of claim 23, wherein the pharmaceutical composition is present in one or more unit dosages.

25. A method of treating an individual having cancer, comprising:
administering to an individual having cancer a therapeutically effective amount of a knottin-drug conjugate of claim 1.

26. The method according to claim 25, wherein the individual has a cancer selected from the group consisting of: brain cancer, breast cancer, ovarian cancer, and pancreatic cancer.

27. A method of making a knottin-drug conjugate, comprising:
conjugating a chemotherapeutic nucleoside drug to a knottin peptide comprising an engineered loop that binds to a receptor on a cancer cell surface, wherein the chemotherapeutic nucleoside drug is conjugated to the knottin peptide through an intracellularly cleavable linker.

28. The knottin-drug conjugate of claim 1, wherein the intracellularly cleavable linker is an enzyme-labile linker.

29. The knottin-drug conjugate of claim 28, wherein the intracellularly cleavable linker is cleavable by a lysosomal protease.

30. The knottin-drug conjugate of claim 29, wherein the intracellularly cleavable linker is cleavable by cathepsin or plasmin.

31. The method according to claim 25, wherein the intracellularly cleavable linker is an enzyme-labile linker.

32. The knottin-drug conjugate of claim 12, wherein the nucleoside analogue is selected from the group consisting of: an adenoside/deoxyadenosine analogue, a guanosine/deoxyguanosine analogue, a thymidine/deoxythymidine analogue, and a deoxyuridine analogue.

33. The knottin-drug conjugate of claim 15, wherein the dipeptide-based intracellularly cleavable linker is a maleimidocaproyl-valine-citruline-p-aminobenzyl (MC-vc-PAB)-based intracellularly cleavable linker.

* * * * *

SEQUENCE LISTING

<160> NUMBER OF SEQ ID NOS: 41

<210> SEQ ID NO 1
<211> LENGTH: 28
<212> TYPE: PRT
<213> ORGANISM: Artificial sequence
<220> FEATURE:
<223> OTHER INFORMATION: synthetic polypeptide

<400> SEQUENCE: 1

Gly Cys Pro Arg Ile Leu Met Arg Cys Lys Gln Asp Ser Asp Cys Leu
1               5                   10                  15

Ala Gly Cys Val Cys Gly Pro Asn Gly Phe Cys Gly
            20                  25

<210> SEQ ID NO 2
<211> LENGTH: 34
<212> TYPE: PRT
<213> ORGANISM: Artificial sequence
<220> FEATURE:
<223> OTHER INFORMATION: synthetic polypeptide

<400> SEQUENCE: 2

Cys Val Arg Leu His Glu Ser Cys Leu Gly Gln Gln Val Pro Cys Cys
1               5                   10                  15

Asp Pro Ala Ala Thr Cys Tyr Cys Arg Phe Phe Asn Ala Phe Cys Tyr
            20                  25                  30

Cys Arg

<210> SEQ ID NO 3
<211> LENGTH: 29
<212> TYPE: PRT
<213> ORGANISM: Artificial sequence
<220> FEATURE:
<223> OTHER INFORMATION: synthetic polypeptide

<400> SEQUENCE: 3

Cys Gly Glu Thr Cys Val Gly Gly Thr Cys Asn Thr Pro Gly Cys Thr
1               5                   10                  15

Cys Ser Trp Pro Val Cys Thr Arg Asn Gly Leu Pro Val
            20                  25

<210> SEQ ID NO 4
<211> LENGTH: 34
<212> TYPE: PRT
<213> ORGANISM: Artificial sequence
<220> FEATURE:
<223> OTHER INFORMATION: synthetic polypeptide

<400> SEQUENCE: 4

Ser Gly Ser Asp Gly Gly Val Cys Pro Lys Ile Leu Lys Lys Cys Arg
1               5                   10                  15

Arg Asp Ser Asp Cys Pro Gly Ala Cys Ile Cys Arg Gly Asn Gly Tyr
            20                  25                  30

Cys Gly

<210> SEQ ID NO 5
<211> LENGTH: 36
<212> TYPE: PRT
<213> ORGANISM: Artificial sequence
<220> FEATURE:
<223> OTHER INFORMATION: synthetic polypeptide

<400> SEQUENCE: 5

```
Met Cys Met Pro Cys Phe Thr Thr Asp His Gln Met Ala Arg Lys Cys
1               5                   10                  15

Asp Asp Cys Cys Gly Gly Lys Gly Arg Gly Lys Cys Tyr Gly Pro Gln
            20                  25                  30

Cys Leu Cys Arg
        35

<210> SEQ ID NO 6
<211> LENGTH: 33
<212> TYPE: PRT
<213> ORGANISM: Artificial sequence
<220> FEATURE:
<223> OTHER INFORMATION: synthetic polypeptide

<400> SEQUENCE: 6

Gly Cys Pro Gln Gly Arg Gly Asp Trp Ala Pro Thr Ser Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 7
<211> LENGTH: 33
<212> TYPE: PRT
<213> ORGANISM: Artificial sequence
<220> FEATURE:
<223> OTHER INFORMATION: synthetic polypeptide

<400> SEQUENCE: 7

Gly Cys Pro Arg Pro Arg Gly Asp Asn Pro Pro Leu Thr Cys Ser Gln
1               5                   10                  15

Asp Ser Asp Cys Leu Ala Gly Cys Val Cys Gly Pro Asn Gly Phe Cys
            20                  25                  30

Gly

<210> SEQ ID NO 8
<211> LENGTH: 33
<212> TYPE: PRT
<213> ORGANISM: Artificial sequence
<220> FEATURE:
<223> OTHER INFORMATION: synthetic polypeptide

<400> SEQUENCE: 8

Gly Cys Ala Glu Pro Arg Gly Asp Met Pro Trp Thr Trp Cys Lys Gln
1               5                   10                  15

Asp Ser Asp Cys Leu Ala Gly Cys Val Cys Gly Pro Asn Gly Phe Cys
            20                  25                  30

Gly

<210> SEQ ID NO 9
<211> LENGTH: 33
<212> TYPE: PRT
<213> ORGANISM: Artificial sequence
<220> FEATURE:
<223> OTHER INFORMATION: synthetic polypeptide

<400> SEQUENCE: 9

Gly Cys Val Gly Gly Arg Gly Asp Trp Ser Pro Lys Trp Cys Lys Gln
1               5                   10                  15

Asp Ser Asp Cys Pro Ala Gly Cys Val Cys Gly Pro Asn Gly Phe Cys
            20                  25                  30
```

```
<210> SEQ ID NO 10
<211> LENGTH: 33
<212> TYPE: PRT
<213> ORGANISM: Artificial sequence
<220> FEATURE:
<223> OTHER INFORMATION: synthetic polypeptide

<400> SEQUENCE: 10

Gly Cys Ala Glu Leu Arg Gly Asp Arg Ser Tyr Pro Glu Cys Lys Gln
1               5                   10                  15

Asp Ser Asp Cys Leu Ala Gly Cys Val Cys Gly Pro Asn Gly Phe Cys
            20                  25                  30

Gly

<210> SEQ ID NO 11
<211> LENGTH: 33
<212> TYPE: PRT
<213> ORGANISM: Artificial sequence
<220> FEATURE:
<223> OTHER INFORMATION: synthetic polypeptide

<400> SEQUENCE: 11

Gly Cys Arg Leu Pro Arg Gly Asp Val Pro Arg Pro His Cys Lys Gln
1               5                   10                  15

Asp Ser Asp Cys Gln Ala Gly Cys Val Cys Gly Pro Asn Gly Phe Cys
            20                  25                  30

Gly

<210> SEQ ID NO 12
<211> LENGTH: 33
<212> TYPE: PRT
<213> ORGANISM: Artificial sequence
<220> FEATURE:
<223> OTHER INFORMATION: synthetic polypeptide

<400> SEQUENCE: 12

Gly Cys Tyr Pro Leu Arg Gly Asp Asn Pro Tyr Ala Ala Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 13
<211> LENGTH: 33
<212> TYPE: PRT
<213> ORGANISM: Artificial sequence
<220> FEATURE:
<223> OTHER INFORMATION: synthetic polypeptide

<400> SEQUENCE: 13

Gly Cys Thr Ile Gly Arg Gly Asp Trp Ala Pro Ser Glu Cys Lys Gln
1               5                   10                  15

Asp Ser Asp Cys Leu Ala Gly Cys Val Cys Gly Pro Asn Gly Phe Cys
            20                  25                  30

Gly

<210> SEQ ID NO 14
<211> LENGTH: 33
<212> TYPE: PRT
```

<213> ORGANISM: Artificial sequence
<220> FEATURE:
<223> OTHER INFORMATION: synthetic polypeptide

<400> SEQUENCE: 14

Gly Cys His Pro Pro Arg Gly Asp Asn Pro Pro Val Thr Cys Lys Gln
1               5                   10                  15

Asp Ser Asp Cys Leu Ala Gly Cys Val Cys Gly Pro Asn Gly Phe Cys
            20                  25                  30

Gly

<210> SEQ ID NO 15
<211> LENGTH: 33
<212> TYPE: PRT
<213> ORGANISM: Artificial sequence
<220> FEATURE:
<223> OTHER INFORMATION: synthetic polypeptide

<400> SEQUENCE: 15

Gly Cys Pro Glu Pro Arg Gly Asp Asn Pro Pro Ser Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 16
<211> LENGTH: 33
<212> TYPE: PRT
<213> ORGANISM: Artificial sequence
<220> FEATURE:
<223> OTHER INFORMATION: synthetic polypeptide

<400> SEQUENCE: 16

Gly Cys Leu Pro Pro Arg Gly Asp Asn Pro Pro Ser Cys Lys Gln
1               5                   10                  15

Asp Ser Asp Cys Gln Ala Gly Cys Val Cys Gly Pro Asn Gly Phe Cys
            20                  25                  30

Gly

<210> SEQ ID NO 17
<211> LENGTH: 33
<212> TYPE: PRT
<213> ORGANISM: Artificial sequence
<220> FEATURE:
<223> OTHER INFORMATION: synthetic polypeptide

<400> SEQUENCE: 17

Gly Cys His Leu Gly Arg Gly Asp Trp Ala Pro Val Gly Cys Lys Gln
1               5                   10                  15

Asp Ser Asp Cys Pro Ala Gly Cys Val Cys Gly Pro Asn Gly Phe Cys
            20                  25                  30

Gly

<210> SEQ ID NO 18
<211> LENGTH: 33
<212> TYPE: PRT
<213> ORGANISM: Artificial sequence
<220> FEATURE:
<223> OTHER INFORMATION: synthetic polypeptide

<400> SEQUENCE: 18

Gly Cys Asn Val Gly Arg Gly Asp Trp Ala Pro Ser Glu Cys Lys Gln

```
                1               5                   10                  15
Asp Ser Asp Cys Pro Ala Gly Cys Val Cys Gly Pro Asn Gly Phe Cys
            20                  25                  30

Gly

<210> SEQ ID NO 19
<211> LENGTH: 33
<212> TYPE: PRT
<213> ORGANISM: Artificial sequence
<220> FEATURE:
<223> OTHER INFORMATION: synthetic polypeptide

<400> SEQUENCE: 19

Gly Cys Phe Pro Gly Arg Gly Asp Trp Ala Pro Ser Ser Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 20
<211> LENGTH: 33
<212> TYPE: PRT
<213> ORGANISM: Artificial sequence
<220> FEATURE:
<223> OTHER INFORMATION: synthetic polypeptide

<400> SEQUENCE: 20

Gly Cys Pro Leu Pro Arg Gly Asp Asn Pro Pro Thr Glu Cys Lys Gln
1               5                   10                  15

Asp Ser Asp Cys Gln Ala Gly Cys Val Cys Gly Pro Asn Gly Phe Cys
            20                  25                  30

Gly

<210> SEQ ID NO 21
<211> LENGTH: 33
<212> TYPE: PRT
<213> ORGANISM: Artificial sequence
<220> FEATURE:
<223> OTHER INFORMATION: synthetic polypeptide

<400> SEQUENCE: 21

Gly Cys Ser Glu Ala Arg Gly Asp Asn Pro Arg Leu Ser Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 22
<211> LENGTH: 33
<212> TYPE: PRT
<213> ORGANISM: Artificial sequence
<220> FEATURE:
<223> OTHER INFORMATION: synthetic polypeptide

<400> SEQUENCE: 22

Gly Cys Leu Leu Gly Arg Gly Asp Trp Ala Pro Glu Ala Cys Lys Gln
1               5                   10                  15

Asp Ser Asp Cys Arg Ala Gly Cys Val Cys Gly Pro Asn Gly Phe Cys
            20                  25                  30

Gly
```

<210> SEQ ID NO 23
<211> LENGTH: 33
<212> TYPE: PRT
<213> ORGANISM: Artificial sequence
<220> FEATURE:
<223> OTHER INFORMATION: synthetic polypeptide

<400> SEQUENCE: 23

```
Gly Cys His Val Gly Arg Gly Asp Trp Ala Pro Leu Lys Cys Lys Gln
1               5                   10                  15

Asp Ser Asp Cys Gln Ala Gly Cys Val Cys Gly Pro Asn Gly Phe Cys
            20                  25                  30

Gly
```

<210> SEQ ID NO 24
<211> LENGTH: 33
<212> TYPE: PRT
<213> ORGANISM: Artificial sequence
<220> FEATURE:
<223> OTHER INFORMATION: synthetic polypeptide

<400> SEQUENCE: 24

```
Gly Cys Val Arg Gly Arg Gly Asp Trp Ala Pro Pro Ser Cys Lys Gln
1               5                   10                  15

Asp Ser Asp Cys Pro Ala Gly Cys Val Cys Gly Pro Asn Gly Phe Cys
            20                  25                  30

Gly
```

<210> SEQ ID NO 25
<211> LENGTH: 33
<212> TYPE: PRT
<213> ORGANISM: Artificial sequence
<220> FEATURE:
<223> OTHER INFORMATION: synthetic polypeptide

<400> SEQUENCE: 25

```
Gly Cys Leu Gly Gly Arg Gly Asp Trp Ala Pro Pro Ala Cys Lys Gln
1               5                   10                  15

Asp Ser Asp Cys Arg Ala Gly Cys Val Cys Gly Pro Asn Gly Phe Cys
            20                  25                  30

Gly
```

<210> SEQ ID NO 26
<211> LENGTH: 33
<212> TYPE: PRT
<213> ORGANISM: Artificial sequence
<220> FEATURE:
<223> OTHER INFORMATION: synthetic polypeptide

<400> SEQUENCE: 26

```
Gly Cys Phe Val Gly Arg Gly Asp Trp Ala Pro Leu Thr Cys Lys Gln
1               5                   10                  15

Asp Ser Asp Cys Gln Ala Gly Cys Val Cys Gly Pro Asn Gly Phe Cys
            20                  25                  30

Gly
```

<210> SEQ ID NO 27
<211> LENGTH: 33
<212> TYPE: PRT
<213> ORGANISM: Artificial sequence
<220> FEATURE:
<223> OTHER INFORMATION: synthetic polypeptide

<400> SEQUENCE: 27

Gly Cys Pro Val Gly Arg Gly Asp Trp Ser Pro Ala Ser Cys Lys Gln
1               5                   10                  15

Asp Ser Asp Cys Arg Ala Gly Cys Val Cys Gly Pro Asn Gly Phe Cys
            20                  25                  30

Gly

<210> SEQ ID NO 28
<211> LENGTH: 33
<212> TYPE: PRT
<213> ORGANISM: Artificial sequence
<220> FEATURE:
<223> OTHER INFORMATION: synthetic polypeptide

<400> SEQUENCE: 28

Gly Cys Pro Arg Pro Arg Gly Asp Asn Pro Pro Leu Thr Cys Lys Gln
1               5                   10                  15

Asp Ser Asp Cys Leu Ala Gly Cys Val Cys Gly Pro Asn Gly Phe Cys
            20                  25                  30

Gly

<210> SEQ ID NO 29
<211> LENGTH: 33
<212> TYPE: PRT
<213> ORGANISM: Artificial sequence
<220> FEATURE:
<223> OTHER INFORMATION: synthetic polypeptide

<400> SEQUENCE: 29

Gly Cys Tyr Gln Gly Arg Gly Asp Trp Ser Pro Ser Ser Cys Lys Gln
1               5                   10                  15

Asp Ser Asp Cys Pro Ala Gly Cys Val Cys Gly Pro Asn Gly Phe Cys
            20                  25                  30

Gly

<210> SEQ ID NO 30
<211> LENGTH: 33
<212> TYPE: PRT
<213> ORGANISM: Artificial sequence
<220> FEATURE:
<223> OTHER INFORMATION: synthetic polypeptide

<400> SEQUENCE: 30

Gly Cys Ala Pro Gly Arg Gly Asp Trp Ala Pro Ser Glu Cys Lys Gln
1               5                   10                  15

Asp Ser Asp Cys Gln Ala Gly Cys Val Cys Gly Pro Asn Gly Phe Cys
            20                  25                  30

Gly

<210> SEQ ID NO 31
<211> LENGTH: 33
<212> TYPE: PRT
<213> ORGANISM: Artificial sequence
<220> FEATURE:
<223> OTHER INFORMATION: synthetic polypeptide

<400> SEQUENCE: 31

Gly Cys Val Gln Gly Arg Gly Asp Trp Ser Pro Ser Ser Cys Lys Gln
1               5                   10                  15

Asp Ser Asp Cys Pro Ala Gly Cys Val Cys Gly Pro Asn Gly Phe Cys

-continued

```
                20                  25                  30
Gly

<210> SEQ ID NO 32
<211> LENGTH: 33
<212> TYPE: PRT
<213> ORGANISM: Artificial sequence
<220> FEATURE:
<223> OTHER INFORMATION: synthetic polypeptide

<400> SEQUENCE: 32

Gly Cys His Val Gly Arg Gly Asp Trp Ala Pro Glu Glu Cys Lys Gln
1               5                   10                  15

Asp Ser Asp Cys Gln Ala Gly Cys Val Cys Gly Pro Asn Gly Phe Cys
                20                  25                  30

Gly

<210> SEQ ID NO 33
<211> LENGTH: 33
<212> TYPE: PRT
<213> ORGANISM: Artificial sequence
<220> FEATURE:
<223> OTHER INFORMATION: synthetic polypeptide

<400> SEQUENCE: 33

Gly Cys Asp Gly Gly Arg Gly Asp Trp Ala Pro Pro Ala Cys Lys Gln
1               5                   10                  15

Asp Ser Asp Cys Arg Ala Gly Cys Val Cys Gly Pro Asn Gly Phe Cys
                20                  25                  30

Gly

<210> SEQ ID NO 34
<211> LENGTH: 33
<212> TYPE: PRT
<213> ORGANISM: Artificial sequence
<220> FEATURE:
<223> OTHER INFORMATION: synthetic polypeptide

<400> SEQUENCE: 34

Gly Cys Pro Gln Gly Arg Gly Asp Trp Ala Pro Glu Trp Cys Lys Gln
1               5                   10                  15

Asp Ser Asp Cys Pro Ala Gly Cys Val Cys Gly Pro Asn Gly Phe Cys
                20                  25                  30

Gly

<210> SEQ ID NO 35
<211> LENGTH: 33
<212> TYPE: PRT
<213> ORGANISM: Artificial sequence
<220> FEATURE:
<223> OTHER INFORMATION: synthetic polypeptide

<400> SEQUENCE: 35

Gly Cys Pro Arg Gly Arg Gly Asp Trp Ser Pro Pro Ala Cys Lys Gln
1               5                   10                  15

Asp Ser Asp Cys Gln Ala Gly Cys Val Cys Gly Pro Asn Gly Phe Cys
                20                  25                  30

Gly

<210> SEQ ID NO 36
<211> LENGTH: 38
```

```
<212> TYPE: PRT
<213> ORGANISM: Artificial sequence
<220> FEATURE:
<223> OTHER INFORMATION: synthetic polypeptide

<400> SEQUENCE: 36

Gly Cys Val Arg Leu His Glu Ser Cys Leu Gly Gln Gln Val Pro Cys
1               5                   10                  15

Cys Asp Pro Ala Ala Thr Cys Tyr Cys Ser Gly Arg Gly Asp Asn Asp
            20                  25                  30

Leu Val Cys Tyr Cys Arg
        35

<210> SEQ ID NO 37
<211> LENGTH: 38
<212> TYPE: PRT
<213> ORGANISM: Artificial sequence
<220> FEATURE:
<223> OTHER INFORMATION: synthetic polypeptide

<400> SEQUENCE: 37

Gly Cys Val Arg Leu His Glu Ser Cys Leu Gly Gln Gln Val Pro Cys
1               5                   10                  15

Cys Asp Pro Ala Ala Thr Cys Tyr Cys Lys Gly Arg Gly Asp Ala Arg
            20                  25                  30

Leu Gln Cys Tyr Cys Arg
        35

<210> SEQ ID NO 38
<211> LENGTH: 38
<212> TYPE: PRT
<213> ORGANISM: Artificial sequence
<220> FEATURE:
<223> OTHER INFORMATION: synthetic polypeptide

<400> SEQUENCE: 38

Gly Cys Val Arg Leu His Glu Ser Cys Leu Gly Gln Gln Val Pro Cys
1               5                   10                  15

Cys Asp Pro Ala Ala Thr Cys Tyr Cys Val Gly Arg Gly Asp Asp Asn
            20                  25                  30

Leu Lys Cys Tyr Cys Arg
        35

<210> SEQ ID NO 39
<211> LENGTH: 38
<212> TYPE: PRT
<213> ORGANISM: Artificial sequence
<220> FEATURE:
<223> OTHER INFORMATION: synthetic polypeptide

<400> SEQUENCE: 39

Gly Cys Val Arg Leu His Glu Ser Cys Leu Gly Gln Gln Val Pro Cys
1               5                   10                  15

Cys Asp Pro Ala Ala Thr Cys Tyr Cys Glu Gly Arg Gly Asp Arg Asp
            20                  25                  30

Met Lys Cys Tyr Cys Arg
        35

<210> SEQ ID NO 40
<211> LENGTH: 38
<212> TYPE: PRT
<213> ORGANISM: Artificial sequence
<220> FEATURE:
```

```
<223> OTHER INFORMATION: synthetic polypeptide

<400> SEQUENCE: 40

Gly Cys Val Arg Leu His Glu Ser Cys Leu Gly Gln Gln Val Pro Cys
1               5                   10                  15

Cys Asp Pro Ala Ala Thr Cys Tyr Cys Tyr Gly Arg Gly Asp Asn Asp
                20                  25                  30

Leu Arg Cys Tyr Cys Arg
            35

<210> SEQ ID NO 41
<211> LENGTH: 33
<212> TYPE: PRT
<213> ORGANISM: Artificial sequence
<220> FEATURE:
<223> OTHER INFORMATION: synthetic polypeptide
<220> FEATURE:
<221> NAME/KEY: MISC_FEATURE
<222> LOCATION: (15)..(15)
<223> OTHER INFORMATION: Xaa represents an unnatural amino acid.

<400> SEQUENCE: 41

Gly Cys Pro Arg Pro Arg Gly Asp Asn Pro Pro Leu Thr Cys Xaa Gln
1               5                   10                  15

Asp Ser Asp Cys Leu Ala Gly Cys Val Cys Gly Pro Asn Gly Phe Cys
                20                  25                  30

Gly
```